United States Patent [19]
Beiser et al.

[11] Patent Number: 5,630,799
[45] Date of Patent: May 20, 1997

[54] FLUID MANAGEMENT SYSTEM

[75] Inventors: David G. Beiser, Brookline; Steven B. Woolfson, Boston, both of Mass.; Kenneth W. Krause, Sandown, N.H.

[73] Assignee: Smith & Nephew Dyonics Inc., Andover, Mass.

[21] Appl. No.: 555,797

[22] Filed: Nov. 9, 1995

Related U.S. Application Data

[63] Continuation of Ser. No. 255,281, Jun. 7, 1994, abandoned, which is a continuation of Ser. No. 867,981, Apr. 13, 1992, abandoned, which is a continuation-in-part of Ser. No. 748,249, Aug. 21, 1991, abandoned, which is a continuation-in-part of Ser. No. 838,465, Feb. 19, 1992, abandoned.

[51] Int. Cl.$^6$ ............................. A61M 31/00; A61M 1/00
[52] U.S. Cl. .................... 604/66; 604/67; 604/151
[58] Field of Search ........................ 604/30, 35, 64–67, 604/151; 128/DIG. 12, DIG. 13

[56] References Cited

U.S. PATENT DOCUMENTS

| | | |
|---|---|---|
| Re. 28,742 | 3/1976 | Rafferty et al. . |
| 2,022,369 | 11/1935 | Curtis . |
| 2,524,764 | 10/1950 | Burke . |
| 3,139,832 | 7/1964 | Saunders . |
| 3,459,183 | 8/1969 | Ring et al. . |
| 3,565,078 | 2/1971 | Vaillancourt et al. . |
| 3,585,996 | 6/1971 | Reynolds et al. . |
| 3,647,324 | 3/1972 | Rafferty et al. . |
| 3,659,587 | 5/1972 | Baldwin . |
| 3,766,916 | 10/1973 | Moorehead et al. . |
| 3,773,046 | 11/1973 | Rosenberg . |
| 3,825,001 | 7/1974 | Bennet et al. . |
| 3,837,381 | 9/1974 | Arroyo . |
| 3,853,127 | 12/1974 | Spademan . |
| 3,864,055 | 2/1975 | Kletschka et al. . |
| 3,900,022 | 8/1975 | Widran . |
| 3,930,505 | 1/1976 | Wallach . |
| 3,957,389 | 5/1976 | Rafferty et al. . |

(List continued on next page.)

FOREIGN PATENT DOCUMENTS

| | | |
|---|---|---|
| 0051718 | 5/1982 | European Pat. Off. . |
| 185658 | 6/1986 | European Pat. Off. . |
| 0362822A3 | 10/1989 | European Pat. Off. . |
| 0370721A3 | 11/1989 | European Pat. Off. . |
| 400587 | 1/1990 | European Pat. Off. . |
| 0417764A1 | 9/1990 | European Pat. Off. . |
| 0437351A1 | 1/1991 | European Pat. Off. . |
| 0532911A1 | 3/1993 | European Pat. Off. . |
| 0541970A1 | 5/1993 | European Pat. Off. . |
| 430890 | 10/1911 | France . |
| 2272633 | 1/1976 | France . |
| 3338758 | 3/1985 | Germany . |
| 52353 | 9/1987 | Ireland . |
| 2065479 | 7/1981 | United Kingdom . |
| 2088215 | 6/1982 | United Kingdom . |
| WO86/00534 | 1/1986 | WIPO . |
| WO86/01390 | 3/1986 | WIPO . |
| WO90/08562 | 8/1990 | WIPO . |
| WO91/15149 | 10/1991 | WIPO . |

OTHER PUBLICATIONS

Brochure: Making Arthroscopy Easier . . . Low Pressure Irrigation System; 1985.
C.D. Morgan et al. Arthroscopy, vol. 3, 1987, pp. 288–291.
Bergstrom & Gillquist, "The Use of an Infusion Pump in Arthroscopy", Arthroscopy: The Journal of Arthroscopic and Related Surgery, 2(1):41–45, (1986).
Optik, Inc., "The Optik Arthropump" Brochure (1989).

*Primary Examiner*—Michael Powell Buiz
*Assistant Examiner*—Nancy Connolly Mulcare
*Attorney, Agent, or Firm*—Fish & Richardson, P.C.

[57] ABSTRACT

Apparatus for supplying liquid to a body cavity during an endoscopic procedure includes a feedback loop-controlled liquid supply device inherently capable of supplying liquid at a substantially constant pressure substantially independent of the flow rate of liquid delivered by the liquid supply device within a relatively wide range of flow rate. Also disclosed are a disposable plastic pump cassette having an inflow pump in a housing, and an operative cannula. The surgical procedure is performed with continuous control over the body cavity pressure, regardless of the outflow flow rate.

7 Claims, 16 Drawing Sheets

U.S. PATENT DOCUMENTS

| | | |
|---|---|---|
| 3,970,408 | 7/1976 | Rafferty et al. . |
| 4,000,739 | 1/1977 | Stevens . |
| 4,007,742 | 2/1977 | Banko . |
| 4,037,984 | 7/1977 | Rafferty et al. . |
| 4,117,843 | 10/1978 | Banko . |
| 4,180,074 | 12/1979 | Murry et al. . |
| 4,194,509 | 3/1980 | Pickering et al. . |
| 4,203,444 | 5/1980 | Bonnell et al. . |
| 4,261,360 | 4/1981 | Perez et al. . |
| 4,263,808 | 4/1981 | Bellotti et al. . |
| 4,314,480 | 2/1982 | Becker . |
| 4,394,862 | 7/1983 | Shim . |
| 4,395,258 | 7/1983 | Wang et al. . |
| 4,423,727 | 1/1984 | Widran et al. . |
| 4,424,833 | 1/1984 | Spector et al. . |
| 4,430,081 | 2/1984 | Timmermans . |
| 4,436,519 | 3/1984 | O'Neill . |
| 4,443,219 | 4/1984 | Meisch et al. . |
| 4,489,750 | 12/1984 | Nehring . |
| 4,491,126 | 1/1985 | Cullor . |
| 4,493,694 | 1/1985 | Wuchinich . |
| 4,496,342 | 1/1985 | Banko ................ 604/27 |
| 4,526,574 | 7/1985 | Pekkarinen . |
| 4,539,998 | 9/1985 | McCord et al. . |
| 4,555,645 | 11/1985 | Atkinson . |
| 4,561,431 | 12/1985 | Atkinson . |
| 4,573,888 | 3/1986 | Kitchin . |
| 4,576,181 | 3/1986 | Wallace et al. . |
| 4,598,579 | 7/1986 | Cummings et al. . |
| 4,604,089 | 8/1986 | Santangelo et al. . |
| 4,610,256 | 9/1986 | Wallace . |
| 4,626,245 | 12/1986 | Weinstein . |
| 4,635,621 | 1/1987 | Atkinson . |
| 4,649,904 | 3/1987 | Krauter et al. . |
| 4,650,462 | 3/1987 | De Santnick et al. . |
| 4,655,197 | 4/1987 | Atkinson . |
| 4,655,752 | 4/1987 | Honkanen et al. . |
| 4,658,829 | 4/1987 | Wallace . |
| 4,662,829 | 5/1987 | Nehring . |
| 4,662,871 | 5/1987 | Rafelson . |
| 4,671,792 | 6/1987 | Borsanyi . |
| 4,673,393 | 6/1987 | Suzuki et al. . |
| 4,679,596 | 7/1987 | Olson . |
| 4,701,160 | 10/1987 | Lindsay et al. . |
| 4,705,508 | 11/1987 | Karnavas et al. ................ 604/113 |
| 4,741,678 | 5/1988 | Nehring . |
| 4,747,826 | 5/1988 | Sassano ................ 604/151 |
| 4,750,902 | 6/1988 | Wuchinich et al. . |
| 4,755,168 | 7/1988 | Romanelli et al. ................ 603/34 |
| 4,778,445 | 10/1988 | Hubbard et al. . |
| 4,781,525 | 11/1988 | Hubbard et al. . |
| 4,785,822 | 11/1988 | Wallace . |
| 4,795,424 | 1/1989 | Burner . |
| 4,795,440 | 1/1989 | Young et al. . |
| 4,798,090 | 1/1989 | Heath et al. . |
| 4,798,594 | 1/1989 | Hillstead . |
| 4,809,679 | 3/1989 | Shimonaka et al. . |
| 4,820,265 | 4/1989 | DeSatnick et al. . |
| 4,838,865 | 6/1989 | Flank et al. . |
| 4,873,986 | 10/1989 | Wallace . |
| 4,900,302 | 2/1990 | Newton ................ 604/30 |
| 4,902,277 | 2/1990 | Mathies et al. . |
| 4,909,798 | 3/1990 | Fleischhacker et al. . |
| 4,929,235 | 5/1990 | Merry et al. . |
| 4,935,005 | 6/1990 | Haines . |
| 4,940,457 | 7/1990 | Olson . |
| 4,949,723 | 8/1990 | Wallace et al. . |
| 4,960,412 | 10/1990 | Fink . |
| 4,973,311 | 11/1990 | Iwakoshi et al. . |
| 4,994,035 | 2/1991 | Mokroe . |
| 4,998,914 | 3/1991 | Wiest et al. . |
| 5,000,733 | 3/1991 | Mathies et al. . |
| 5,000,745 | 3/1991 | Guest et al. . |
| 5,011,469 | 4/1991 | Buckberg et al. . |
| 5,037,386 | 8/1991 | Marcus et al. . |
| 5,041,095 | 8/1991 | Littrell . |
| 5,053,002 | 10/1991 | Barlow ................ 604/30 |
| 5,098,384 | 3/1992 | Abrams . |
| 5,098,387 | 3/1992 | Wiest et al. . |
| 5,147,305 | 9/1992 | Nakamura et al. . |
| 5,152,746 | 10/1992 | Atkinson et al. ................ 604/67 |
| 5,176,629 | 1/1993 | Kullas et al. . |
| 5,176,648 | 1/1993 | Holmes et al. . |
| 5,176,652 | 1/1993 | Littrell . |

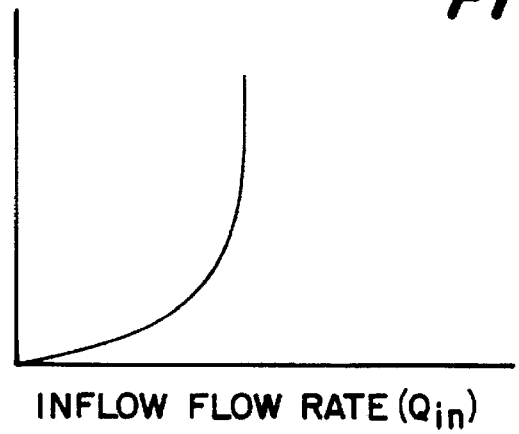
FIG. 3
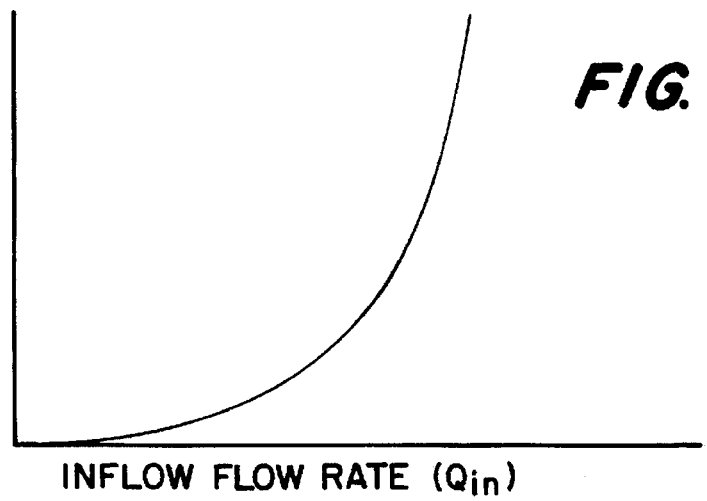
FIG. 4
FIG. 5

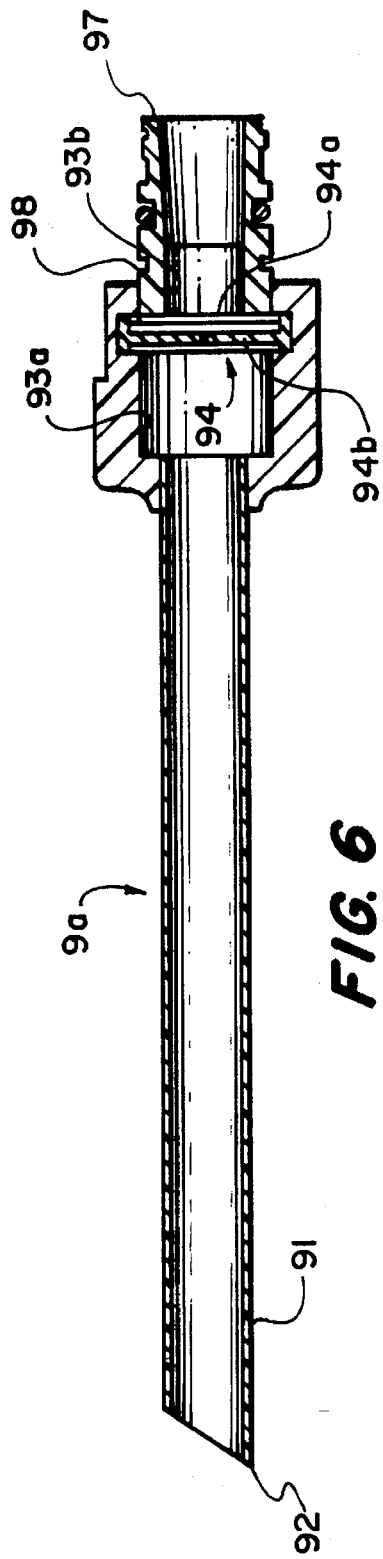
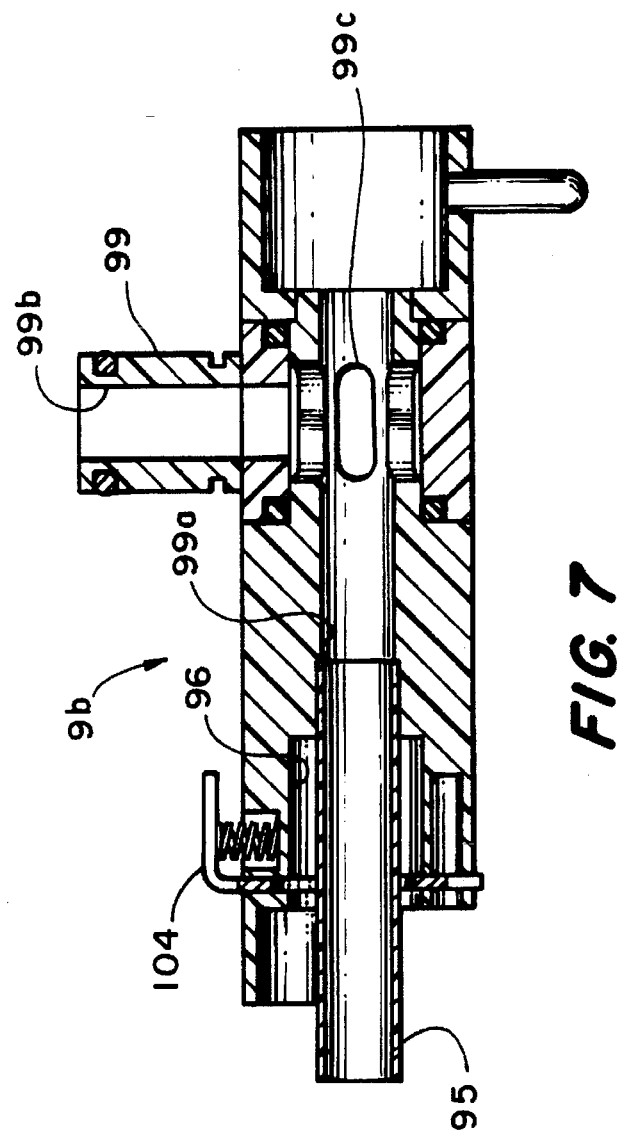

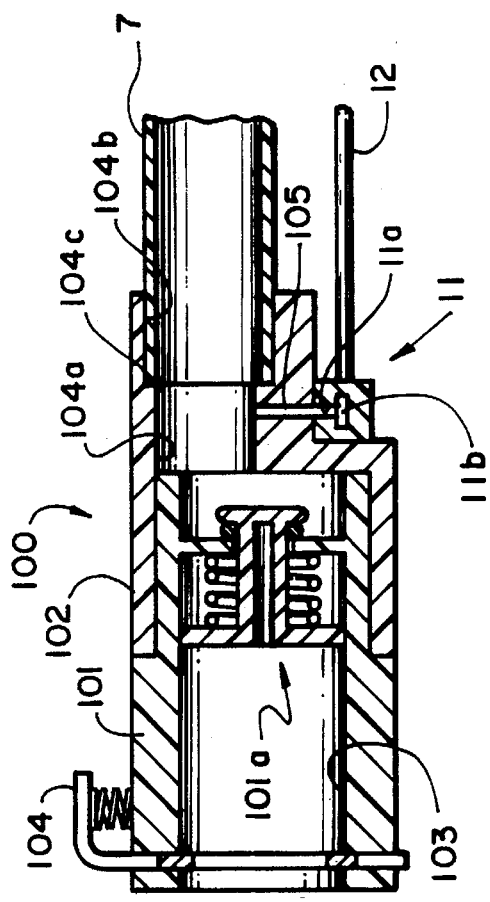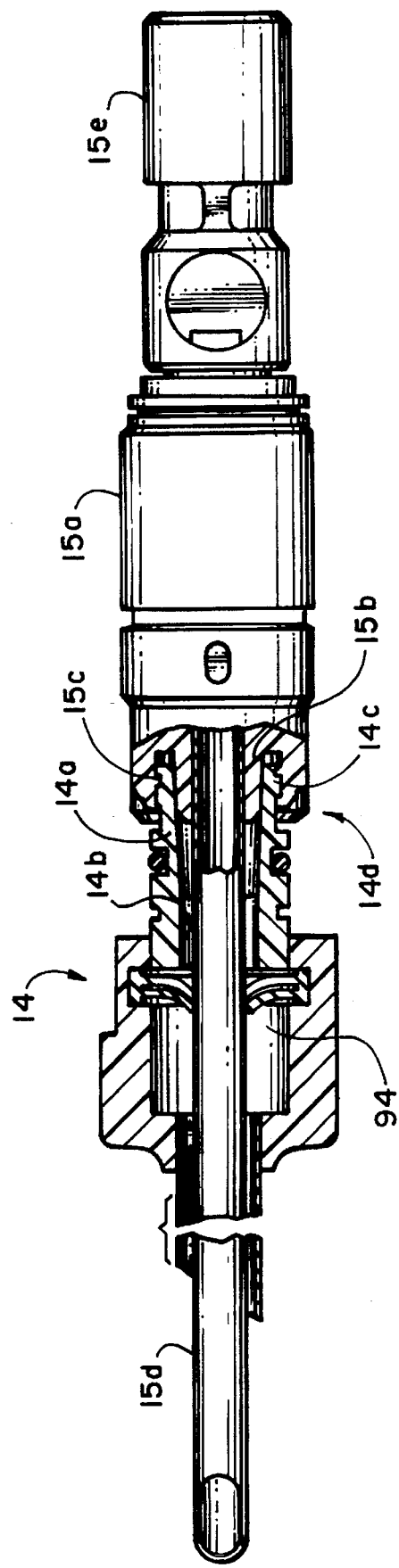

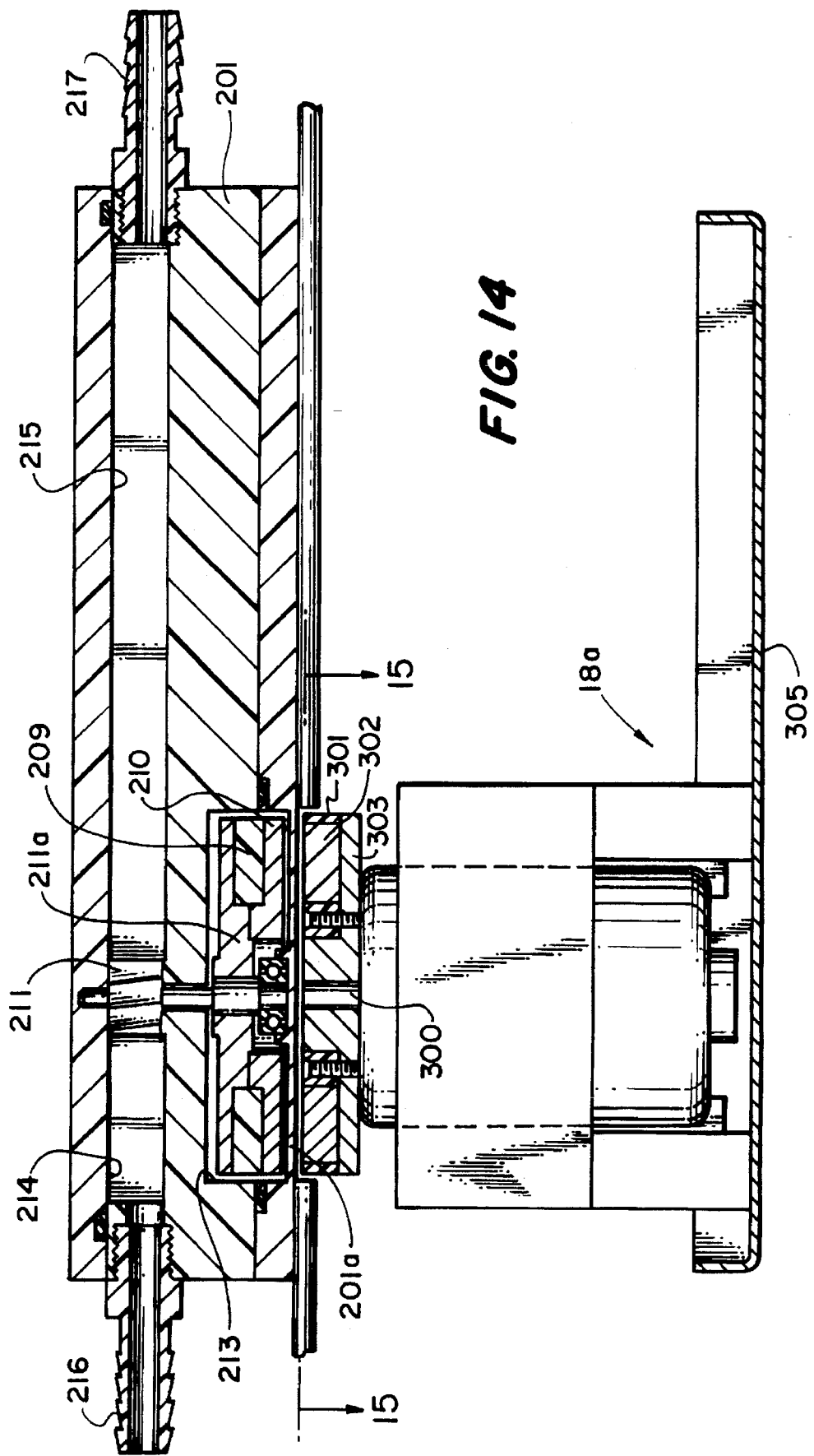

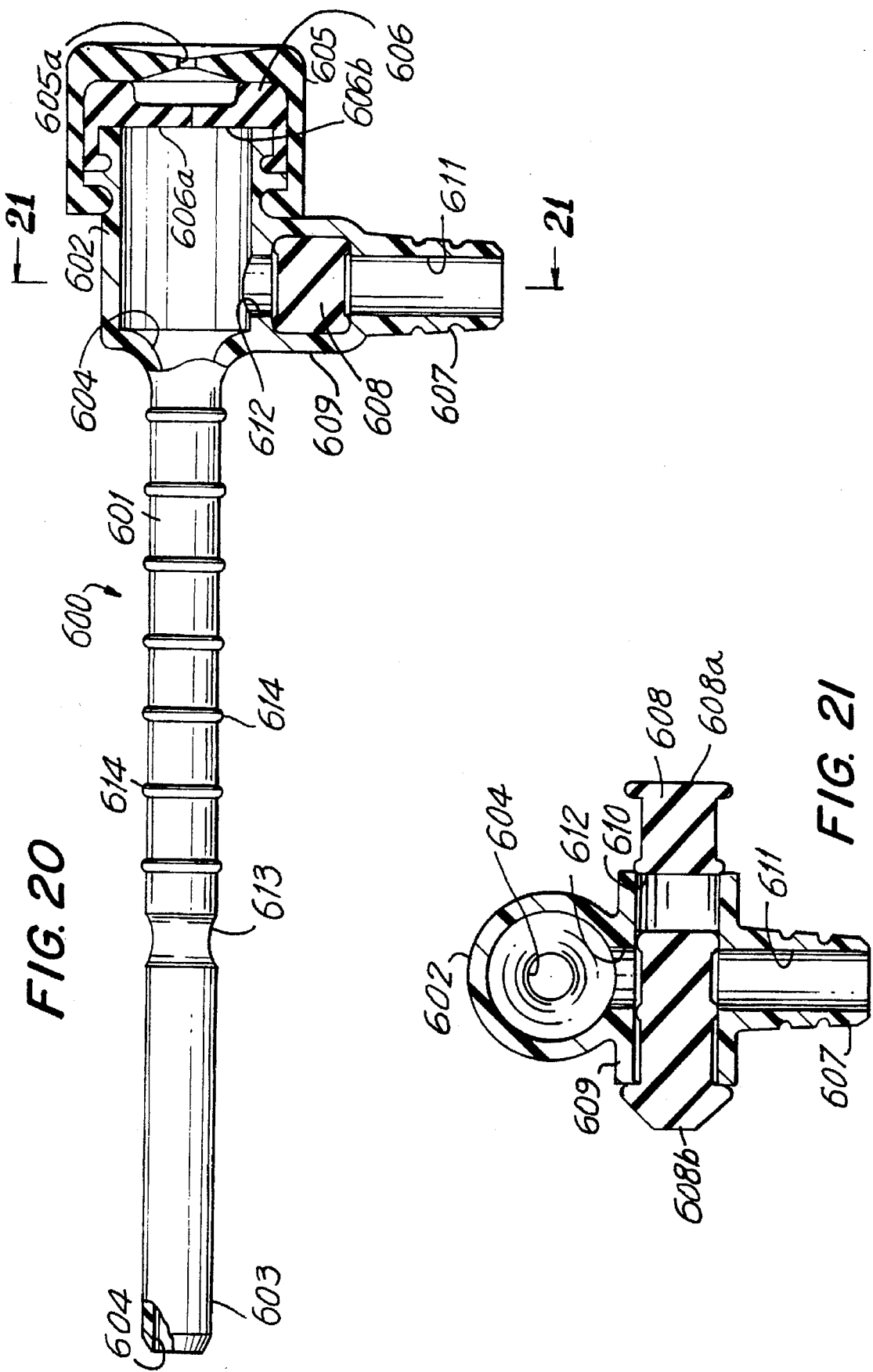

FLUID MANAGEMENT SYSTEM

This is a continuation of application Ser. No. 08/255,281, filed Jun. 7, 1994, now abandoned, which is a continuation of Ser. No. 07/867,981, filed Apr. 13, 1992, now abandoned, which is a continuation-in-part of Ser. No. 07/748,249, filed Aug. 21, 1991, now abandoned, which is a continuation-in-part of Ser. No. 07/838,465, filed Feb. 19, 1992, now abandoned.

The present invention relates to apparatus for supplying liquid under pressure to a body cavity during an endoscopic procedure, and more particularly to an improved arthroscopic pump apparatus.

Pumping systems have been previously proposed for supplying liquid under pressure to a body cavity by means of an inflow pump during an endoscopic procedure, such as arthroscopic surgery. Two prior art arthroscopic pumping systems are illustrative, namely that of DeSatnick et al. U.S. Pat. No. 4,650,642, issued Mar. 17, 1987 and Mathies et al. U.S. Pat. No. 4,902,277, issued Feb. 20, 1990. DeSatnick et al. propose the use of an open loop displacement pump as the inflow pump and an open loop suction pump as the outflow pump. Mathies et al. propose the use of a feedback loop controlled inflow pump and an open loop suction pump that is automatically switched between an outflow cannula and a tool.

Displacement pumps operate by providing volumes of fluid as a function of pump speed regardless of the outlet pressure of the pump. Thus, even at low pump speeds, displacement pumps are capable of generating pressures that can be too high, e.g., where the outflow from the pressurized body cavity is curtailed by blockages or the like. The present invention provides a safer system by utilizing a liquid supply means whose outflow flow rate is inherently inversely responsive to changes in the body cavity pressure. Preferably, the liquid supply means is inherently capable of supplying liquid at a substantially constant pressure substantially independent of the flow rate of liquid delivered by the liquid supply means within a relatively wide range of flow rate. The liquid supply means of the invention, when regulated by a feedback loop responsive to the pressure in the body cavity, can provide precise control of body cavity pressure regardless of changes in the volume of the body cavity or changes in the outflow flow rate from the body cavity, such as flow through a surgical tool, leakage or blockage or otherwise.

The liquid supply means may be a reservoir of liquid that is isometrically pressurized. Preferably, the liquid supply means is a dynamic pump means, such as a centrifugal pump. As used throughout the present application, the terms "dynamic pump" and "displacement pump" are as defined in the classification of pumps set forth in Pump Handbook, Edited by I. J. Karassik et al., Second Edition, McGraw-Hill Book Company, pages 1.2–1.5, which is incorporated herein by reference thereto. A dynamic pump used in the present invention preferably provides a constant pressure head in a manner substantially insensitive to variations in flow rate.

The apparatus of the present invention may include a suction pump for aspirating liquid from the body cavity. Alternatively, liquid may be aspirated from the body cavity from a suction source, such as wall suction. According to the present invention, outflow flow rate is independent of body cavity pressure and instead is chosen to optimize the performance of the surgical tool being used. The combination of a dynamic inflow (or irrigation) pump, such as a centrifugal inflow pump, controlled in response to body cavity pressure and an open loop aspiration of liquid from the body cavity provides a safe, stable, pressure-limited control system.

It is a particular advantage of the present invention that it is preferably a two-portal system. That is, only two cannulas are inserted into the surgical site, an inflow cannula for the endoscope and an outflow cannula for the surgical tool. Liquid under pressure is normally supplied to the body cavity by the liquid supply means through the annulus between the inflow cannula and an endoscope in the cannula, while liquid is aspirated from the surgical site by suction via the outflow cannula or a surgical tool inserted into the outflow cannula. Alternatively, inflow liquid can be supplied via an endoscope having an internal conduit for supplying liquid to the body cavity. While not presently preferred, outflow liquid can simply drain from the outflow cannula. Moreover, body cavity pressure is calculated from the output of a pressure sensor in communication with the inflowing liquid at a location upstream of the body cavity, thus eliminating the need for a third portal for a pressure sensor inserted into the body cavity. In one embodiment of the invention, the pressure sensor is closely adjacent the body cavity, for example at the connection of an endoscope to the tubing supplying inflow liquid to the body cavity via the endoscope. In a presently preferred embodiment of the invention, the pressure sensor senses pressure at the outlet of the inflow pump located within a disposable cassette.

The present invention also provides a disposable cassette containing the inflow pump means. The cassette may also include an outflow suction pump means. Preferably, the cassette will also include a resilient tubing that may be connected in series with conduit means for aspirating liquid from the body cavity such that crimping of the resilient tubing means restricts the flow of liquid aspirated from the body cavity. The cassette is preferably provided with a thin, flexible diaphragm in liquid communication with the outlet of the inflow pump means.

The present invention also provides an operative cannula that can serve as the outflow cannula. The cannula is provided with a sealing means at its proximal end for sealingly engaging tools passing through the sealing means proximally to distally and distally to proximally. Preferably, the operative cannula can be cut to provide a shorter cannula with a tapered distal end.

The present invention is illustrated in terms of its preferred embodiments in the accompanying drawings, in which:

FIG. 3 is a curve showing the relationship between the pressure drop from the pressure sensing means to the inflow cannula and the inflow flow rate;

FIG. 4 is a family of curves showing the relationship between the inflow pump pressure and the inflow flow rate at various pump speeds;

FIG. 5 is a curve showing the relationship between the pressure drop from the inflow pump to the pressure sensing means and the inflow flow rate;

FIG. 6 is a view in section of an operative cannula;

FIG. 7 is a view in section of an irrigation extender;

FIG. 9 is a detail view in section of a pressure sensing means;

FIG. 10 is a view in section of a blade of a surgical tool inserted in the operative cannula;

FIG. 14 is a view in section taken along lines 14—14 in FIG. 11;

FIG. 20 is a plan view, partly in section, of an operative cannula of the invention;

FIG. 21 is a view in section taken along lines 21—21 in FIG. 20;

Figure 1:
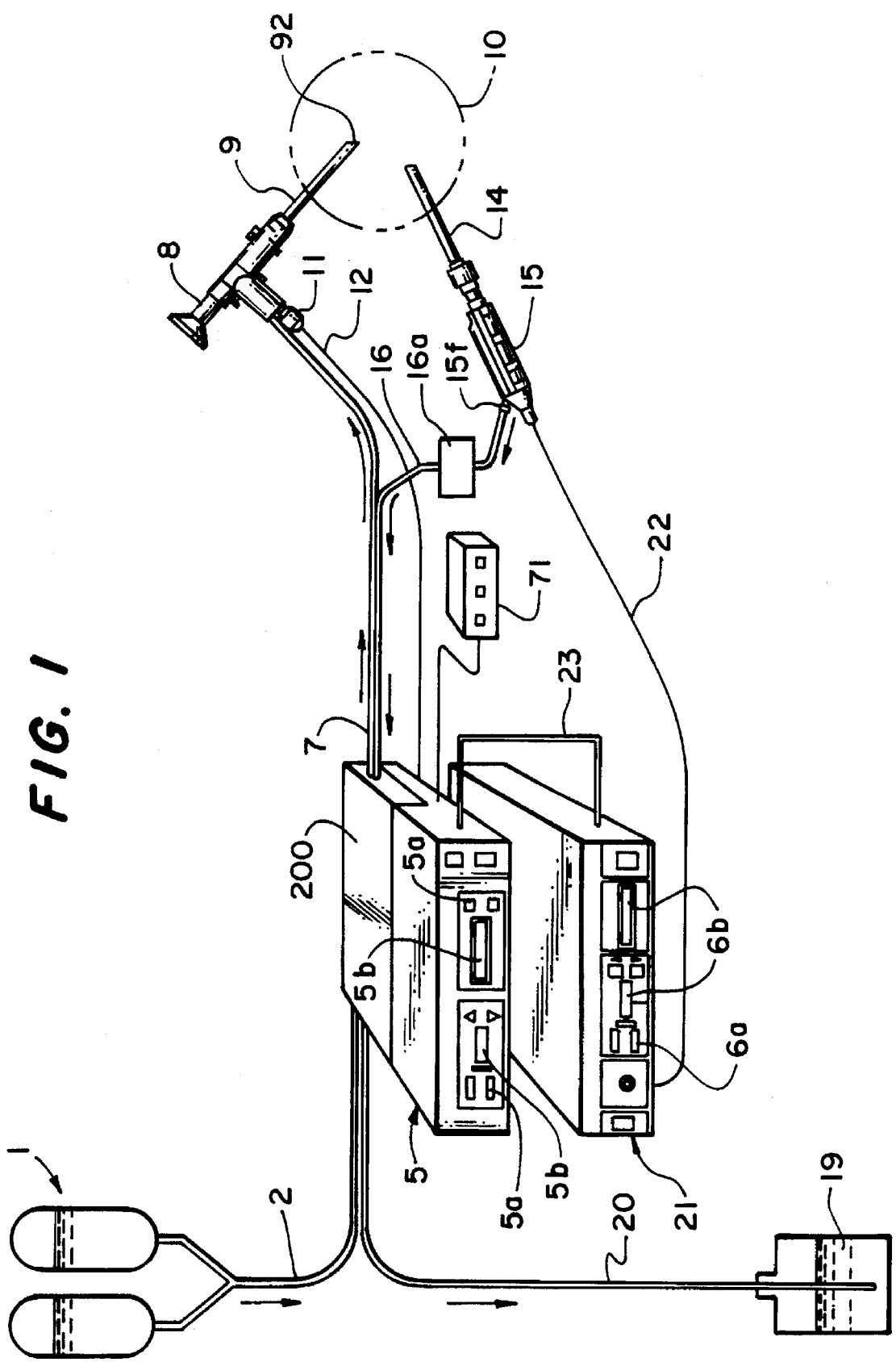
FIG. 1 is a schematic illustration of the apparatus of the invention.

Referring to FIG. 1, the apparatus of the present invention includes a fluid source 1, usually two bags of sterile saline, communicating via conduit 2 with the inlet of a centrifugal inflow pump 4 (FIG. 2) housed within a cassette 200 in fluid management unit 5. Centrifugal inflow pump 4 supplies liquid under pressure through its outlet to conduit 7 and thence to the body cavity 10. As will be discussed in detail hereinafter, inflow cannula assembly 9 is inserted into body cavity 10 and endoscope 8 is placed within inflow cannula assembly 9 such that liquid under pressure is delivered by centrifugal inflow pump 4 to body cavity 10 via the annulus between the endoscope 8 and the inflow cannula assembly 9.

Pressure transducer 11 is located upstream of the body cavity 10 and senses the liquid pressure in conduit 7 as will be described in detail hereinafter. In the embodiment of the invention shown in FIGS. 1 and 2, pressure transducer 11 is at the connection between conduit 7 and endoscope 8. The output from pressure transducer 11 is sent via line 12 to a pressure signal processor 13 (FIG. 2) within fluid management unit 5 for computing the pressure within body cavity 10. The desired pressure for the body cavity will be set by operating a selector 5a on fluid management unit 5 and display 5b will display the set pressure. Pressure controller 40 (FIG. 2) within fluid management unit 5 is responsive to the body cavity pressure signal generated by pressure signal processor 13 to adjust the speed of centrifugal inflow pump 4 to increase or decrease the outlet pressure of the liquid delivered by centrifugal inflow pump 4 and thereby maintain the body cavity pressure at the desired set value, as will be explained in detail hereinafter.

An outflow cannula 14 (described in detail hereinafter) is inserted into the body cavity 10. Tool 15 is inserted via outflow conduit 14 into the body cavity 10, and the surgeon will manipulate tool 15 while viewing the procedure via endoscope 8, as is conventional. Tool control unit 21 powers tool 15 via power cord 22. Outflow conduit 16 connects the inlet of a suction pump 18 (FIG. 2) within unit 5 with the outlet of tool 15, whereby liquid within body cavity 10 may be aspirated and sent to waste container 19 via conduit 20. Fluid exiting body cavity 10 is filtered by tissue trap 16a located upstream of suction pump 18.

Endoscope 8 and tool 15 are reused after sterilization. It is presently preferred that the pumps 4 and 18, the pressure transducer 11, and the conduits are disposable, as well as the blades for the tool 15.

During the preoperative stage, the surgeon will select a desired pressure for the body cavity for the given surgical procedure by operating a set-pressure selector 5a, thereby causing set pressure generator 30 (FIG. 2) to generate a set pressure signal 31, which is applied to an input of pressure controller 40. To the other input of pressure controller 40 is applied signal 32a corresponding to the pressure in body cavity 10.

Body cavity pressure signal 32a may be calculated by pressure signal processor 13 using a lumped parameter model as follows. By empirically determining the pressure vs. flow characteristics of each of the components in the path of fluid flow, (from fluid source 1 to distal end 92 (FIG. 1) of inflow assembly 9), one can determine body cavity pressure by calculating pressure drops across each component. One method takes into account the individual pressure vs. flow characteristics of centrifugal inflow pump 4, conduit 7 and inflow cannula assembly 9. While this will require more demanding software calculations, it will allow easier theoretical modeling of the effects of changing the pressure vs. flow characteristics of any component. Another method lumps the pressure vs. flow characteristics of the inflow pump 4 and conduit 7 up to the point of pressure measurement by transducer 11. This method simplifies the calculation of the body cavity pressure, but it is specific to the design of the inflow pump and conduit 7. Either method may be used in the present invention.

For either method, the body cavity pressure, $P_c$, is calculated by subtracting the pressure drop across the inflow cannula assembly 9 from the pressure, $P_s$, sensed by transducer 11. The pressure drop across inflow cannula assembly 9, ($P_s$–$P_c$), was empirically determined for various flows, $Q_{in}$, by measuring the pressure at the outlet 92 of inflow cannula assembly 9 at a given flow, $Q_{in}$, and subtracting it from the sensed pressure, $P_s$, at that flow. A typical curve plotting ($P_s$–$P_c$) versus flow is schematically shown in FIG. 3, and was accurately fit using the function:

(1) $P_s - P_c = A_1 Q_{in}^2 + A_2 Q_{in}$ where $A_1$ and $A_2$ are constants, which can be rewritten as:

(2) $P_c = P_s - A_1 Q_{in}^2 - A_2 Q_{in}$

The values for constants $A_1$ and $A_2$ are determined and stored in memory for use by pressure signal processor 13.

A more generic method used to determine cavity pressure calculates the inflow, $Q_{in}$, by solving two simultaneous nonlinear equations as follows. The relationship between inflow, $Q_{in}$, and pump pressure, $P_p$, can be determined empirically by plotting $P_p$ vs. $Q_{in}$ for the inlet pump 4 for a range of pump speeds, (RPM). A family of curves was obtained for $P_p$ vs. $Q_{in}$ over a range of pump speeds (RPM), and is schematically shown in FIG. 4. For a given RPM, and using a centrifugal inflow pump connected to fluid source 1 via conduit 2 of 0.25 inch ID and 90 inches long and made of PVC, the equation was determined to be:

(3) $P_p = B_0 + B_1 Q_{in}^2 + B_2 Q_{in}$ which can be rewritten as:

$$Q_{in}=\frac{-B_2+\sqrt{B_2^2+4B_1(B_0-P_p)}}{2B_1} \quad (4)$$

using the assumption that $Q_{in}$ must always be positive.

In this equation, $B_0$ is the constant obtained at zero flow, which includes a component derived from the height of the fluid source (e.g. the bag of saline 1), above the inflow pump 4.

As the speed of motor 4a is varied, the values for $B_n$ change, but the general function does not. By repeating this pressure vs. flow experiment for many different motor speeds, functions are determined for $B_n$ as functions of motor speed. The speed of motor 4a (FIG. 2) can be determined by employing a feedback tachometer, but the actual motor speed is assumed to be a direct function of the pulse width modulation signal 61 (FIG. 2) used to drive motor 4a to be described in detail hereinafter. The functions for each $B_n$ can be expressed as a function of RPM by:

(5) $B_n=f(RPM)$ and RPM can be expressed as a function of the pulse width modulation signal, (PWM), by:

(6) $RPM=C \cdot PWM$

Pressure transducer 11 senses the pressure of liquid in conduit 7 at a point between centrifugal pump 4 and the inflow cannula 9. The relationship between the inflow, $Q_{in}$, and the pressure drop from the centrifugal inflow pump 4 to the transducer 11 can also be determined empirically by measuring $P_p$ (pump outlet pressure) and $P_s$ (sensed pressure) over a range of flow rates and fitting the resulting $(P_p-P_s)$ vs. $Q_{in}$ data, such as schematically shown in FIG. 5, to an equation. Using a conduit 7 of 0.25 inch ID and ten feet long made of PVC, the function was determined to be:

(7) $P_p-P_s=D_1Q_{in}^2+D_2Q_{in}$ which can be rewritten as:

$$Q_{in}=\frac{-D_2+\sqrt{D_2^2-4D_1(P_s-P_p)}}{2D_1} \quad (8)$$

on the assumption that $Q_{in}$ must always be positive.

Given the sensed pressure, $P_s$, and the pulse width modulation signal, (PWM), cavity pressure, $P_c$, is calculated in the following manner:

a) Given PWM, calculate RPM from equation (6);
b) Given RPM, calculate $B_n$ from equation (5);
c) Given $B_n$ and $P_s$, solve equations (4) and (8) for the two unknowns, $Q_{in}$ and $P_p$;
d) Given $P_s$, $A_n$ and $Q_{in}$, calculate $P_c$ from equation (2).

Pressure signal processor 13 may be provided with any suitable algorithm to solve equations (4) and (8) for unknowns $P_p$ and $Q_{in}$. Suitable algorithms are commercially available. Equations (2), (5), and (6) are solved using appropriate software routines of a conventional nature.

Pressure signal processor 13 then generates a signal corresponding to the body cavity pressure, $P_c$, which is sent via lines 32 and 32a to the input of pressure controller 40 and via lines 32 and 32b to a pressure display 5b on the face of fluid management unit 5 (FIG. 1). Processor 13 can generate a signal representing the flow rate, $Q_{in}$, of liquid into the body cavity, which can be sent via line 33 to a display 5b on unit 5 showing the inflow flow rate. If desired, inflow, $Q_{in}$, can be integrated over time to estimate the total volume of liquid infused and the result displayed on unit 5 (not shown), so that the physician can monitor liquid usage and avoid unexpected depletion of the liquid supply. Since the pressure is maintained within narrow limits, $Q_{in}$ can be accurately measured.

Pressure controller 40 compares the set pressure signal applied via line 31 and the calculated body cavity pressure signal applied via line 32a and generates a signal representing a pump speed necessary to raise or lower the calculated body cavity pressure to equal the set pressure. Pressure controller 40 thus sets the speed of motor 4a of centrifugal pump 4 and therefore the output from pressure controller 40 at any given time represents the actual speed of the pump 4 at that time. This pump speed output signal is supplied via lines 41 and 42 to an input of pressure signal processor 13 so that the processor 13 can select the constants $B_n$ of equation (4) using equation (5). That is, processor 13 can be provided with equation (5) for constants $B_n$ as a function of RPM. Cavity pressure $P_c$ can then be calculated using the method described above.

A different and presently preferred method used to calculate cavity pressure, $P_c$, eliminates the need to calculate $Q_{in}$ from $P_p$ and the pressure drop caused by conduit 7. Instead, the pressure vs. flow characteristics of the inflow pump 4 and conduit 7 are lumped together and empirically determined as a single component; therefore, $Q_{in}$ can be determined directly from $P_s$. The pressure vs. flow characteristics of the inflow cannula assembly 9 are as described previously in equation (2):

(2) $P_c=P_s-A_1Q_{in}^2-A_2Q_{in}$

Since $P_s$ is measured, and $A_n$ are predetermined empirically, $P_c$ can be calculated, knowing $Q_{in}$.

To calculate $Q_{in}$, the pressure vs. flow characteristics of inflow pump 4 in communication with conduits 2 and 7 from fluid source 1 to the point of pressure measurement by transducer 11 were determined empirically over a range of speeds of motor 4a. This empirical pressure vs. flow relationship was accurately fit with the following function:

(9) $P_s=E_0-E_1Q_{in}^2-E_2Q_{in}$ which can be rewritten as:

$$Q_{in}=\frac{-E_2+\sqrt{E_2^2-4E_1(P_s-E_0)}}{2E_1} \quad (10)$$

As described above the functions for each $B_n$ can be expressed as functions of RPM by:

(11) $E_n=f(RPM)$ and RPM can be expressed as a function of the pulse width modulation signal, (PWM), by:

(12) $RPM=C \cdot PWM$

Although the value for C in equation (12) is the same as the value for C in equation (6), the values for $E_n$ derived from equation (11) are not the same as the $B_n$ values derived from equation (5).

Given the sensed pressure, $P_s$, and the pulse width modulation signal, (PWM), body cavity pressure, $P_c$, is calculated in the following manner:

a) Given PWM, calculate RPM from equation 12;
b) Given RPM, calculate $E_n$ from equation 11;
c) Given $E_n$ and $P_s$, calculate $Q_{in}$ from equation 10; and d) Given $P_s$, $A_n$ and $Q_{in}$, calculate $P_c$ from equation 2. Equations (2), (10), (11), and (12) can be solved using appropriate software routines of a conventional nature.

AND gates 60a and 60b (FIG. 2) are software conditional statements, but could be implemented in hardware, if desired. To the input of AND gate 60a is applied the pump speed signal via lines 41 and 43. Unless an override signal is provided via line 52 at the other input of AND gate 60a, the pump speed PWM signal is sent via line 61 to a variable speed pump motor 4a to raise or lower the pump speed so that it equals the pump speed represented by the pump speed signal.

A fault condition controller 50 is provided to generate an override signal if any of a number of system faults is detected. To the inputs 50a of controller 50 are applied signals representing faults such as excessive body cavity pressure, excessive inflow, sensor failure, etc. Controller 50 generates a fault signal in a conventional manner, which is sent via lines 51 and 52 to the AND gate 60a and via lines 51 and 53 to the AND gate 60b associated with the suction pump 18. The presence of a fault signal at the input of gates 60a and 60b provides a pump OFF signal as the output of gates 60a and 60b that will shut down motors 4a and 18a of centrifugal inflow pump 4 and suction pump 18, respectively.

Gates 60a, 60b, processor 13 and controllers 40, 50 are preferably provided by a microprocessor.

Tool 15 and tool control unit 21 are preferably provided by the PS 3500 motor drive and PS 3500 EP control unit, respectively, available from Smith & Nephew Dyonics Inc., Andover, Mass. Tool 15 will thus contain a motor, a coupler for accepting a desired surgical blade and an internal passageway for the flow of liquid from the surgical site through the blade and tool to the conduit 16 and thence to suction pump 18. Tool control unit 21 contains a power source and a controller for the tool motor. As is known, the DYONICS PS-3500 control unit stores the ranges of tool motor speeds suitable for each of the DYONICS surgical blades that can be used with the DYONICS PS-3500 motor drive, and automatically displays this range to the surgeon on displays 6b (FIG. 1) after the blade is inserted into the PS-3500 motor drive. The surgeon selects a blade speed within this range by operating selector 6a (FIG. 1). See U.S. Pat. No. 4,705,038, issued Nov. 10, 1987.

Control unit 21 generates output signals representing the blade selected and the speed of the tool motor, the signals being sent via line 23 to lines 23a and 23b (FIG. 2), respectively, and thence to suction pump controller 70. This information is processed by the suction pump controller 70, which sends an output signal representing the desired suction pump motor speed via line 70a to AND gate 60b. If the tool motor is OFF, the suction pump motor may be OFF or run at a low speed, such as up to about 200 RPM. If the tool motor is ON, depending on the blade selected, the suction pump motor speed will be in the range of about 500 to about 4,000 RPM. The suction pump motor speed signal is sent by AND gate 60b to pump motor 18a via line 70b, unless a fault signal has been applied to the input of gate 60b by line 53.

No feedback loop is provided for motor 18a. The outflow rate of liquid is solely a function of the blade used in tool 15 and whether the motor (not shown) of tool 15 is running or idle.

A manual override selector 71 is provided to enable the surgeon to override controller 70 to select a low, medium or high speed for motor 18a for different outflow scenarios. Fault condition controller 50 will also override controller 70 by sending a fault signal via line 53 to an input of AND gate 60b, which will shut down pump motor 18a, as described above.

Figure 6A:
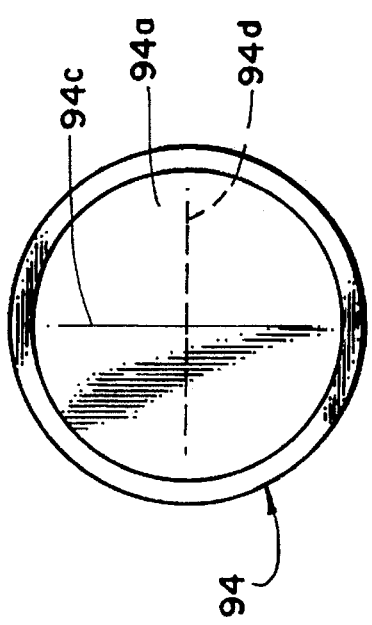
FIG. 6A is an enlarged detail view of the seal in the operative cannula.
Figure 8:
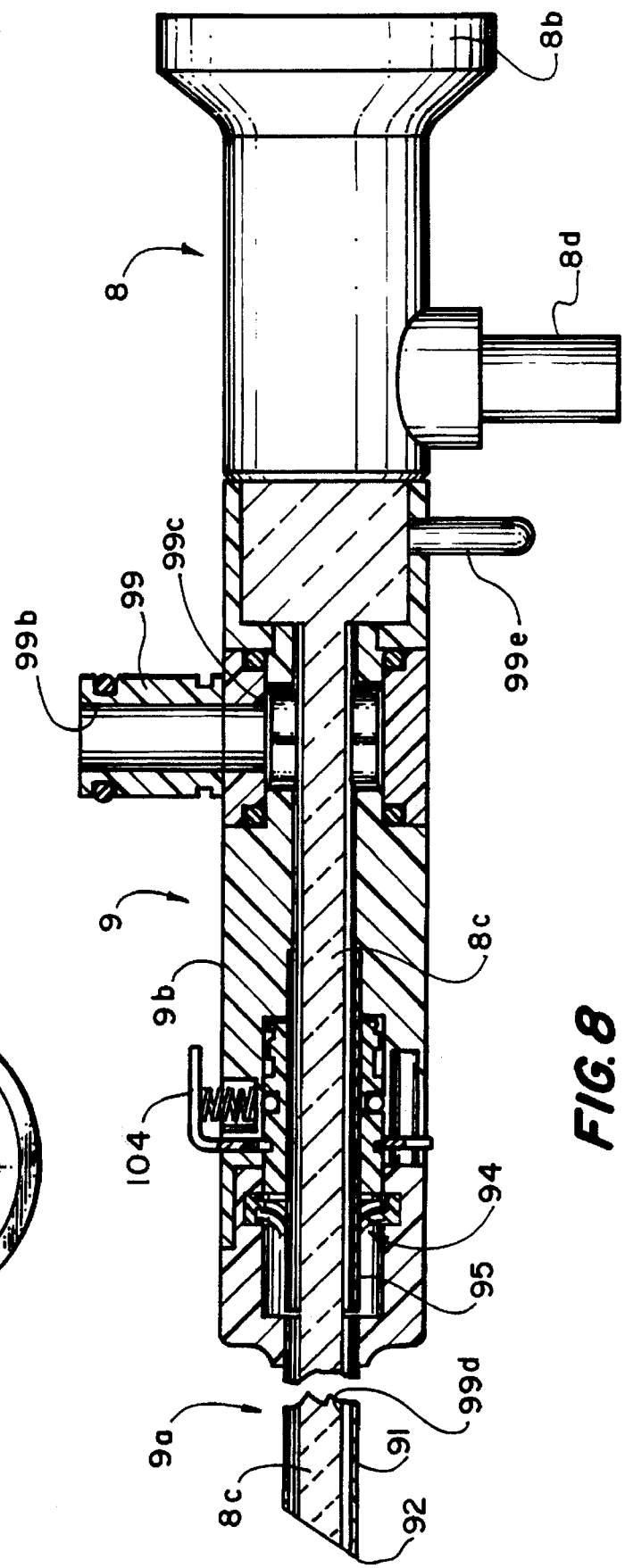
FIG. 8 is a view in section showing the operative cannula and irrigation extender coupled together to form an inflow cannula assembly, with an endoscope inserted in the inflow cannula assembly.

FIGS. 6 and 7 show an operative cannula 9a and irrigation extender 9b that snap together to form the inflow cannula assembly 9 illustrated in FIG. 8. Operative cannula 9a has a needle portion 91 terminating in distal end 92. Bores 93a and 93b are sealed by seal 94, which when opened by seal piercer 95 (FIGS. 7 and 8) of extender 9b, allows fluid to flow through the cannula assembly 9 into body cavity 10.

Extender 9b is provided with bore 96 that receives the proximal end 97 of cannula 9a. Latch 104 snaps into groove 98 of cannula 9a to hold the inflow cannula members 9a, 9b together. Seal 94 (FIG. 6A) has opposed faces 94a, 94b formed of an elastomer with transverse slits 94c, 94d formed therein and an outer mounting ring 94e. Seal 94 may be formed using a removable insert between the faces 94a, 94b. Seal piercer 95 passes through slits 94c, 94d to open the seal; the seal 94 being resealed when extender 9b is uncoupled from cannula 91.

Extender 9b is provided with a rotatably mounted inlet 99 that communicates with the interior bore 99a via inlet bore 99b and apertures 99c. When endoscope 8 (FIG. 8) is inserted into the inflow cannula assembly 9, inflow liquid flows through bore 99b of inlet 99 and exits distal end 92 via apertures 99c and the annulus 99d between the tube 91 of cannula 9a and the endoscope 8.

Endoscope 8 may be secured to extender 9b by a bayonet lock (not shown) using post 99e to facilitate locking of the extender 9b to endoscope 8. Endoscope 8 is a conventional endoscope having eyepiece 8b, light transmitting optics 8c and light inlet 8d.

Referring to FIG. 9, a piezoresistive bridge pressure transducer 11 is carried by connector 100. Commercially available transducers can be used if modified to use biocompatible materials. Connector 100 is formed of a front portion 101 and rear portion 102. Front portion 101 has an internal bore 103 for receiving the inflow inlet 99 of extender 9b, which is held in place by the spring-loaded latch 104 being inserted into groove 98 in inflow inlet 99. Insertion of inflow inlet 99 into bore 103 will also open spring-loaded valve 101a in front unit 101. Rear unit 102 is provided with a stepped bore 104a, 104b connected by shoulder 104c. Transducer 11 is glued to the underside of unit 102 with bore 105 in unit 102 in liquid communication with bore 11a in transducer 11 such that liquid flowing through conduit 7 will fill bores 105 and 11a to come into direct contact with sensing diaphragm 11b of transducer 11. Bores 105 and 11a are of small diameter, such as about 0.04 inches, and diaphragm 11b is hence in contact with a small column of liquid that is at the same pressure as the inflow liquid. Transducer 11 transmits a voltage signal corresponding to the pressure, $P_s$, sensed by diaphragm 11b to processor 13 via line 12.

Of course, pressure transducer 11 can be located anywhere between the pump 4 and body cavity 10, with the body cavity pressure being calculated as described above. If the transducer 11 is located at the pump 4, then only the pressure drop between the pump 4 and cannula tip 92 need be taken into account.

Alternatively, a pressure sensing tube (not shown) may be used, communicating at one end with the body cavity 10 or with conduits 7 or 16 immediately outward of body cavity 10 and utilizing air as the pressure transmission medium, as is known. See, e.g., DeSatnick et al. U.S. Pat. No. 4,650,462. Other pressure sensors may also be used.

In FIG. 10, outflow cannula 14 is shown assembled to blade 15a of a surgical tool 15. Outflow cannula 14 is preferably identical to the operative cannula 9a and has a luer taper 14a in bore 14b and a double lead screw 14c at its proximal end 14d. Blade 15a has a complementary luer taper 15b and double lead thread 15c so that blade 15a can be sealingly fastened to the cannula 14. Tubular portion 15d opens and passes through seal 94. Blade 15a is operatively connected by shank 15e to a tool 15 (FIG. 1). Suction applied by suction pump 18 will aspirate fluid from body cavity 10 through the tubular portion 15d into tool 15. Fluid exits tool 15 via outlet 15f (FIG. 1) into conduit 16.

Figure 11:
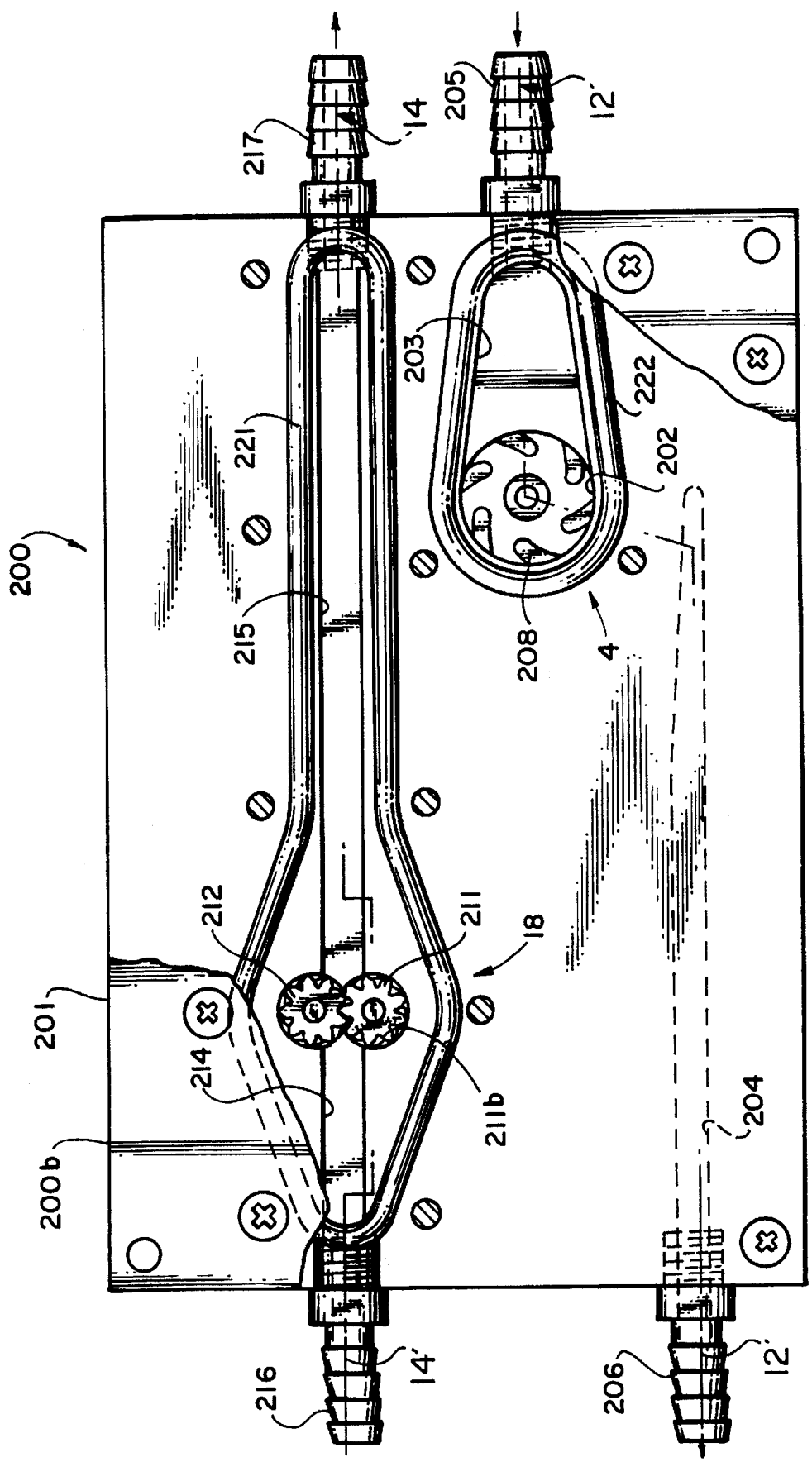
FIG. 11 is a top plan view of a pump cassette of the present invention.
Figure 12:
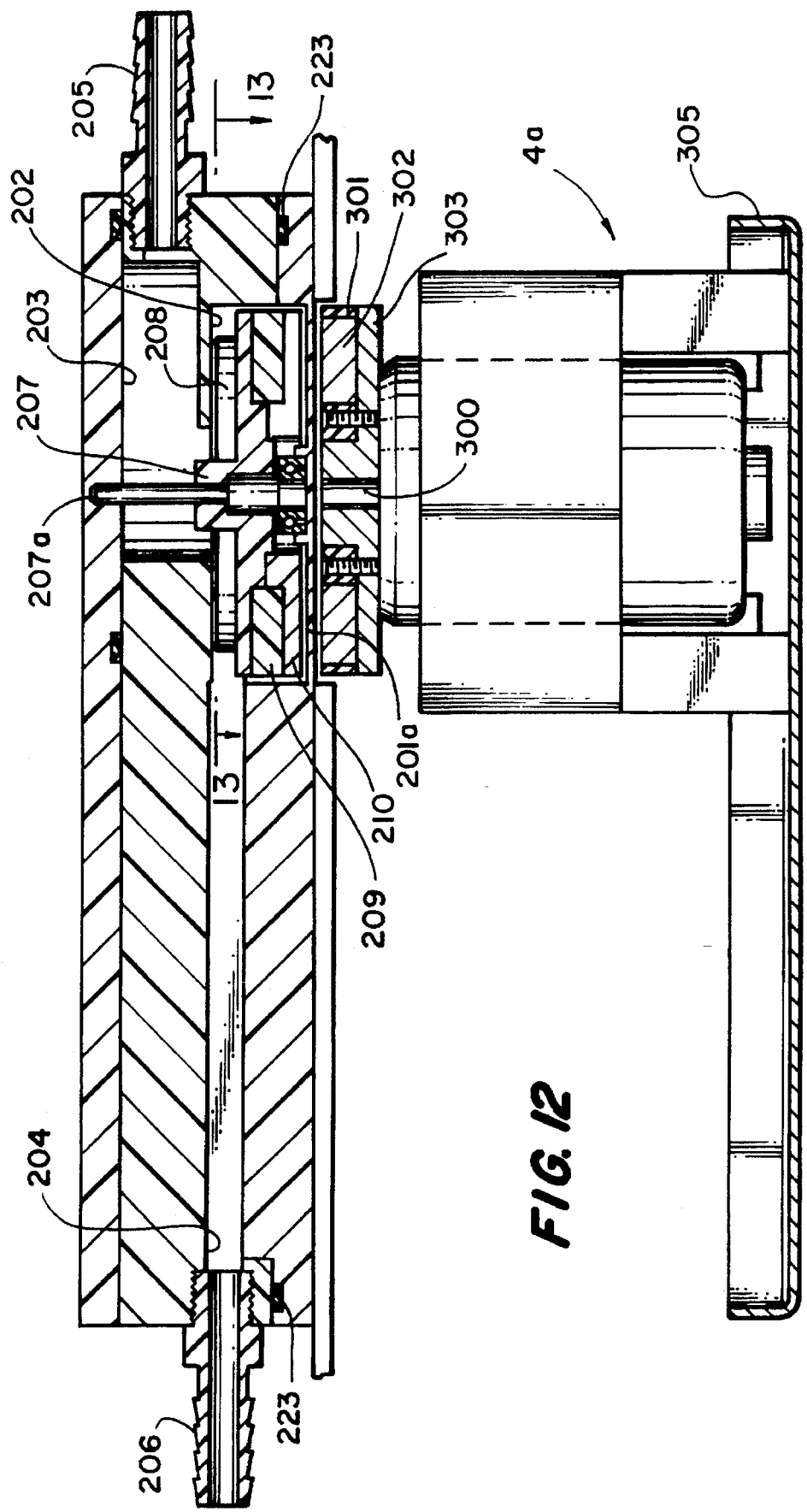
FIG. 12 is a view in section along lines 12—12 in FIG. 11.
Figure 13:
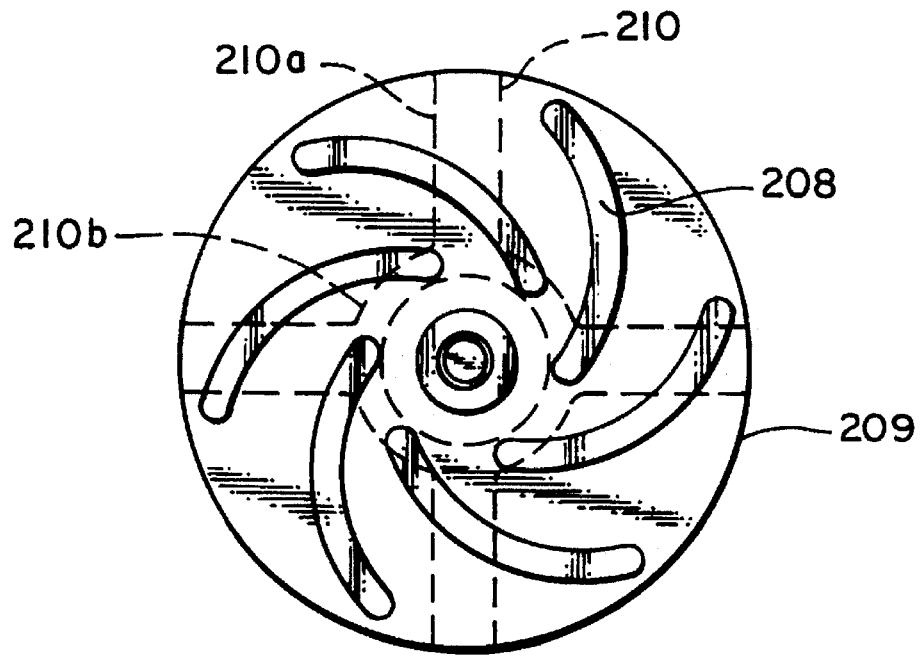
FIG. 13 is a top plan view of the impeller of the centrifugal pump.
Figure 15:
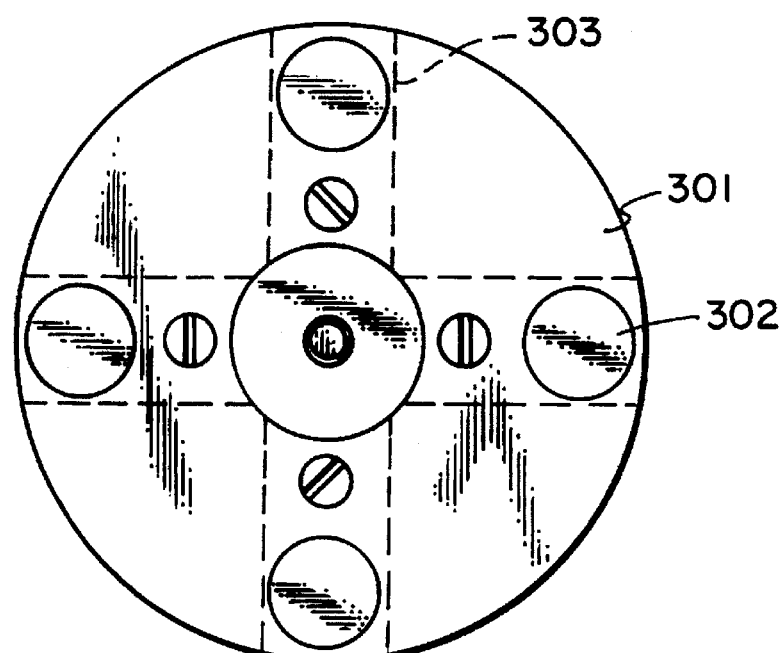
FIG. 15 is a top plan view of one of the motors used to drive the pumps.

FIGS. 11–15 describe a disposable pump cassette 200 containing the centrifugal inflow pump 4 and a gear pump 18 serving to aspirate fluid from body cavity 10. Pumps 4 and 18 are housed in plastic housing 201 having recesses formed therein during the molding of housing 201 to provide a centrifugal pump chamber 202 (FIG. 12), and an inlet conduit 203 and an outlet conduit 204 connected between the centrifugal pump inlet 205 and outlet 206, respectively, and chamber 202. Centrifugal pump impeller 207 is received in chamber 202 and is secured to plastic shaft 207a. Impeller 207 is made of plastic and is provided with curved vanes 208 formed during the molding of impeller 207. Impeller 207 is cemented to plastic spacer 209 and electroless nickel-plated low carbon steel cross-member 210 (FIG. 13). The widths of the arm 210a and hub 210b are empirically determined to maximize the torque imparted to the impeller 207. Impeller assembly 207, 207a, 208, 209, 210 is spaced from the bottom 201a so that it may freely rotate.

Motor 4a is provided with plastic member 301, magnets 302 and iron cross-member 303 that are assembled together and are rotated by shaft 300. Motor 4a is secured to housing 305, which is contained within fluid management unit 5. Magnets 302 are magnetically coupled to the iron cross-member 210 such that impeller 207 will rotate at the same speed as plastic disc 301 when motor 4a is operated to rotate shaft 300 and disc 301.

Suction pump 18 is a displacement pump provided by gears 211, 212. Driving gear 211 is carried by a rotatable plastic rotor 211a (FIG. 14) cemented to plastic spacer 209 and assembled to iron cross-member 210 in the same manner as described above. Driven gear 212 is rotatably mounted in housing 200 by providing a suitable recess for receiving the gearshaft of gear 212.

Housing 201 has recesses therein formed during the molding thereof to provide a cavity 213 for receiving the rotor assembly 211a, 209, 210, a cavity 211b for receiving gear 211 and an inlet conduit 214 and outlet conduit 215 connected between the suction pump inlet 216 and outlet 217, respectively, and cavity 211a. Rotor assembly 211a, 209, 210 is spaced from bottom 201a so that it may freely rotate. Shaft 300 of motor 18a, which is supported on member 305 within fluid management unit 5, carries the disc and magnet assembly 301, 302, 303, so that operation of motor 18a causes rotor 211a and gear 211 to rotate, thereby rotating the meshing gear 212. Fluid is pumped out of outlet 217 by the displacement pumping action of gears 211, 212.

Housing 201 is closed by cover 200b, which is in liquid-sealing engagement with O-rings 221 and 222 (FIG. 11). Bottom 201a sealingly engages O-ring 223 (FIG. 12).

The apparatus of the present invention may be operated as follows. Inflow cannula assembly 9 and outflow cannula 14 are inserted into the body cavity 10, endoscope 8 is inserted into body cavity 10 via inflow cannula assembly 9 and conduit 7 is connected between fluid management unit 5 and the inlet 99 of extender 9b. If the surgeon intends to examine the site before inserting tool 15 into cavity 10, then outflow conduit 16 is preferably connected directly between fluid management unit 5 and outflow cannula 14. In such a case, the appropriate speed for pump 18 is determined by manual override 71. Otherwise, outflow conduit 16 is connected between fluid management unit 5 and the outlet 15f of tool 15 as shown in FIG. 1. In either case, the desired pressure in body cavity 10 is maintained by the feedback loop described above, while the outflow flow rate is determined independently of the pressure in body cavity 10 by the nature of the blade in tool 15 and the speed of the motor in tool 15.

Set pressure generator 30 is then operated to select a pressure suitable for the surgical site. For example, the selected pressure may be within the ranges set forth below:

| Surgical Site | Pressure Range (mmHg) |
| --- | --- |
| Ankle | 80–150 |
| Knee | 35–90 |
| Shoulder | 80–150 |
| Wrist | 30–80 |
| User defined | <150 |

Figure 2:
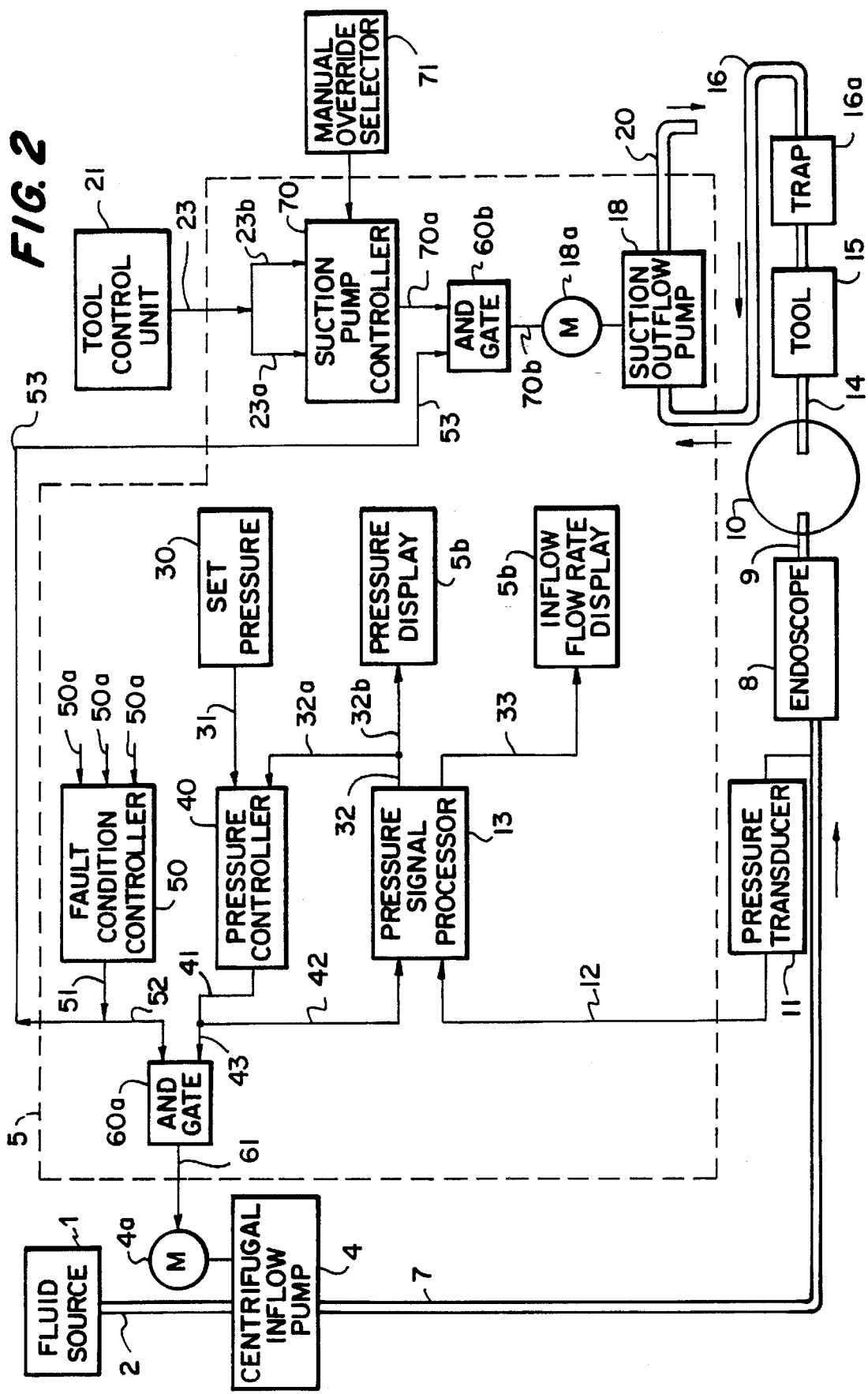
FIG. 2 is a block diagram of a control system of the present invention.
Figure 16:
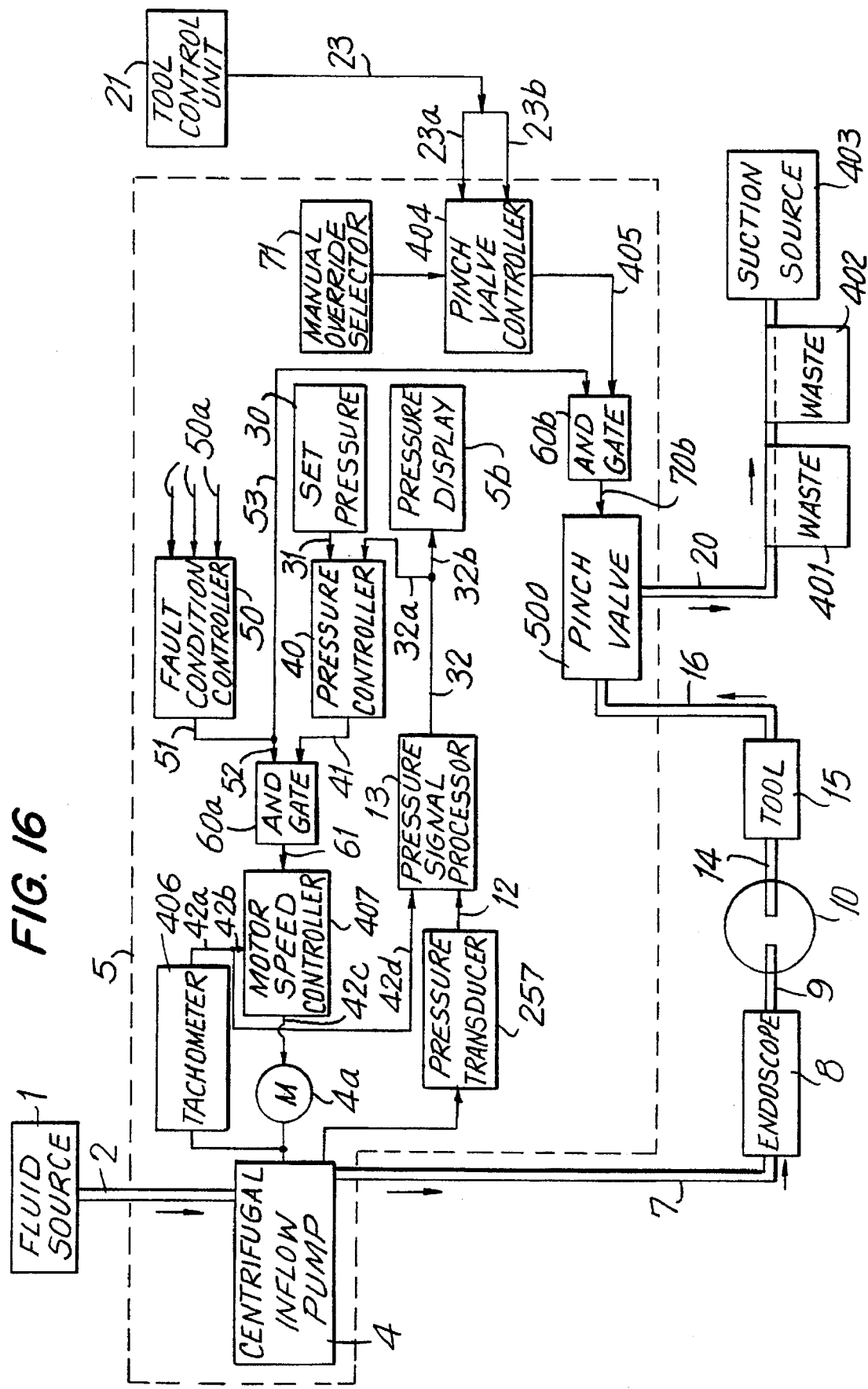
FIG. 16 is a block diagram of another control system of the present invention.

FIG. 16 illustrates a presently preferred embodiment in which some of the elements shown in FIGS. 1 and 2 have been eliminated and/or replaced. In particular, the suction pump 18 has been eliminated from the cassette 200, and the suction pump motor 18a and its associated controls have likewise been eliminated. Other modifications have been made to the system shown in FIG. 2, as will be discussed hereinafter. Those elements from FIG. 2 that have been retained are illustrated in FIG. 16 using the same reference numerals as used in FIG. 2.

Figure 17:
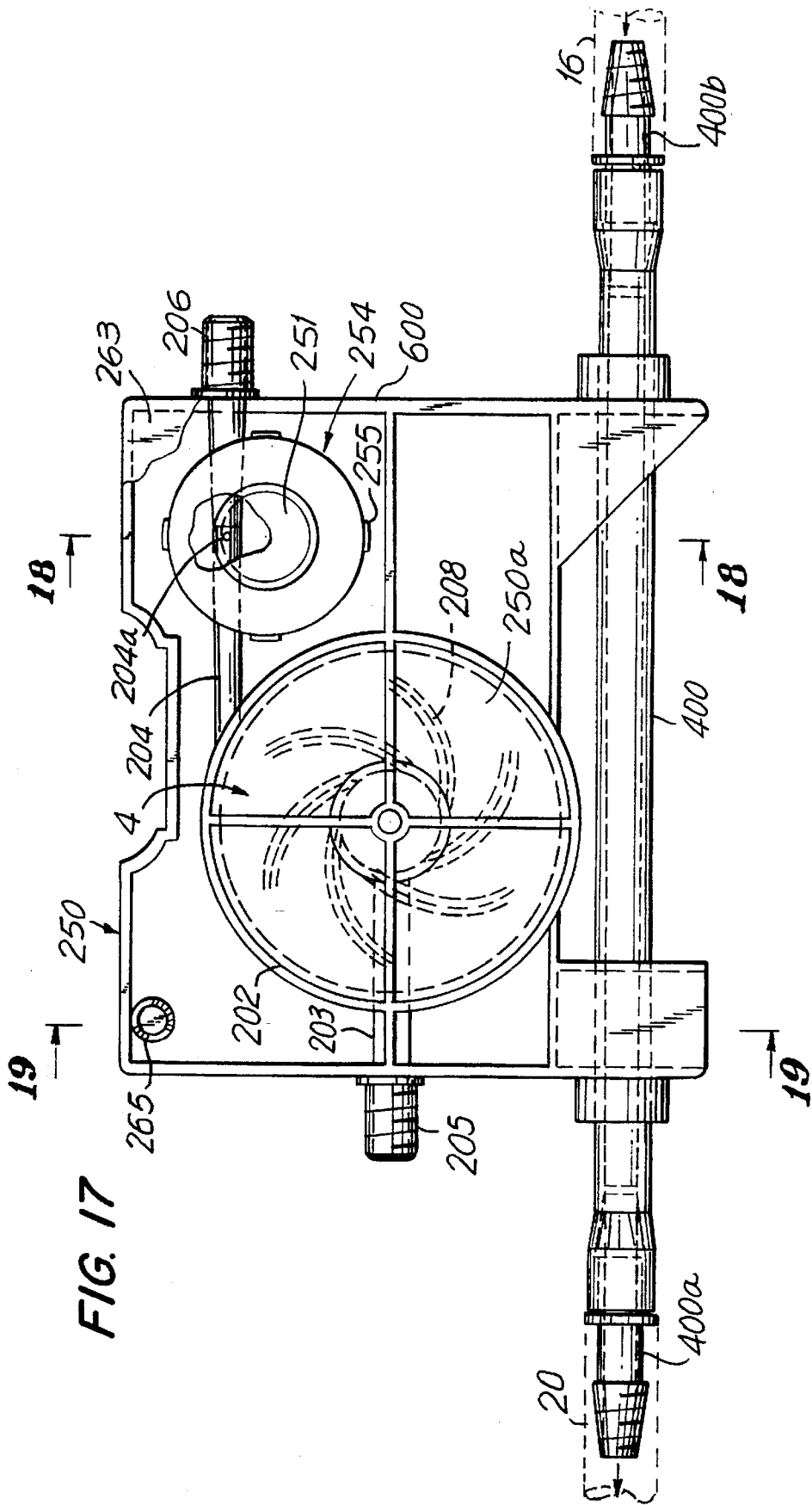
FIG. 17 is a plan view, from the rear, of another pump cassette of the invention.

Referring to FIG. 16, the outlet of tool 15 is connected via tubing 16, 20 and waste containers 401, 402 to a source of suction 403, such as wall suction, whereby liquid may be aspirated from body cavity 10. Connected between the ends of tubing 16, 20 is a length of tubing 400 carried by cassette 250 (FIG. 17). A normally closed pinch valve 500 (FIGS. 19A, 19B) restricts the flow of liquid flowing through tubing 16, 20 by the degree to which the tubing 400 is pinched or crimped. Pinch valve 500 may be set to provide no flow of liquid in its "closed" position or a nominal flow of liquid, as desired. Pinch valve controller 404 will process the output signals in lines 23a, 23b representing the blade selected for tool 15 and the speed of the tool motor and will generate an output signal 405 representing the desired degree of opening of the pinch valve 500, which in turn permits the desired rate of flow of liquid through tubing 400 and tubing 16,20. Output signal 405 will be applied to pinch valve 500 by AND gate 60b via line 70b unless a fault signal has been applied to the input of gate 60b by line 53. Manual override selector 71 allows the surgeon to override the pinch valve controller 404 to select the desired degree of crimping of tubing 400 by pinch valve 500 to thus obtain low, medium or high outflow flow rates through tubing 400 and tubing 16,20.

Suction source 403 aspirates liquid from joint 10 into waste containers 401, 402 connected in series. A suitable number of containers 401, 402 is provided to accommodate the predicted volume of waste liquid. Suction source 403 may be hospital or office wall suction or a stand alone water-aspirator or the like.

FIG. 16 shows that the pressure transducer 257 is upstream of the body cavity 10. As will be described hereinafter, pressure transducer 257 (FIG. 18) is located at the outlet of centrifugal inflow pump 4.

The speed of motor 4a is determined by tachometer 406 and this information is provided via lines 42a and 42b to motor speed controller 407, which also receives the pump speed signal via line 61. Motor speed controller 407 compares the desired motor speed signal to the actual motor speed signal sent by the tachometer 406 and sends a signal to motor 4a via line 42c representing the pump speed necessary to raise or lower the calculated body cavity pressure to equal the set pressure. The motor speed signal is also fed back by tachometer 406 to an input of pressure signal processor 13 via lines 42a,42d.

The presently preferred embodiment of pressure signal processor 13 used in FIG. 16 employs a simplified version of the pressure signal processor described earlier. First, rather than estimating the pump speed using the PWM signal as described above, the pump speed is monitored directly from the tachometer 406 feedback signal, TAC, sent via line 42d. Second, the need to calculate the flow rate, $Q_{in}$, from equations (4) and (8) or from equation (10) was eliminated, thus significantly reducing the time for processor 13 to calculate the estimated body cavity pressure, $P_c$. This was accomplished by using a direct relationship between the flow related pressure drop, $P_1$, upstream of the sensor 257 to the fluid source 1 and the flow related pressure drop, $P_2$, downstream of the sensor 257 to the cannula tip 92.

Another simplification was made because it was empirically determined that, for a given centrifugal pump design, the coefficient $B_0$ in equation 4 and $E_0$ in equation 10 were strictly dependent on TAC and the height of the fluid supply 1 above the pump 4, but were not dependent on flow. The remaining variables $B_1$, $B_2$, $E_1$, and $E_2$ were actually constants that were dependent only on the design of the tubing 2,7 and cannula 9. Since the design of the tubing, cannula and pump are fixed, so will be the associated variables, $B_1$, $B_2$, $E_1$, and $E_2$.

The variables $B_0$ and $E_0$ described previously are dependent on the height of fluid source 1 above pump 4, the pump speed, RPM, and the design of the centrifugal pump 4. Therefore, since the pump design will be fixed and the pump speed is measurable, the height of bags 1 above pump 4 must be either fixed or a measurable variable. Since the presently preferred embodiment fixes the height of fluid supply bag 1 at two feet above pump 4 (45 mmHg), the processor 13 software contains the variable $P_0$ (bag offset) preset to a constant of 45 mmHg, but the bag height offset may be used as a variable input with appropriate change in the processor software.

Given a fixed centrifugal pump design, the peak pressure that the centrifugal pump can generate with no flow through it is a function of tachometer speed, TAC, by:

(A) $P_z = f(TAC) = G_1(TAC)^2 + G_2(TAC)$.

The peak zero flow pressure that the system can generate is also dependent on the fluid supply bag offset, $P_0$; therefore the total zero flow pressure, $P_t$, that the system can generate is defined by:

(B) $P_t = P_z + P_o$.

The pressure drop upstream of the sensor, $P_1$, across the tubing 2 and centrifugal pump 4, is related to the flow through them by, (C) $P_1 = P_t - P_s = H_1 Q_{in}^2 + H_2 Q_{in}$ where $P_s$ is the sensed pressure, and $P_t$ is the total zero flow pressure described earlier. Equation C is the same relationship as equation 9 where $P_t = E_0$, $H_1 = E_1$, and $H_2 = E_2$. The values for $H_1$ and $H_2$ are dependent on the placement of the pressure sensor 257 in the outflow path of the centrifugal pump, the geometry of the centrifugal pump, the geometry of tubing 2 and the size of the spikes (not shown). Because the entire inflow tube set 2 and pump 4 are manufactured under tight tolerancing, it has been found that the values for $H_1$ and $H_2$ do not change significantly from assembly to assembly. Therefore the following pressure conversion algorithm can apply to any such pump and inflow tubeset assembly as long as the values for $A_1$ and $A_2$ in equation 1 and $H_1$ and $H_2$ in equation C are not significantly changed from setup to setup.

The pressure drop, $P_2$, downstream of the sensor across the tubing 7 and cannula 9, is related to the flow through them by equation D, which is the same as equation 1:

(D) $P_2 = P_s - P_c = A_1 Q_{in}^2 + A_2 Q_{in}$ where $P_s$ is the sensed pressure, and $P_c$ is the pressure at the distal end 92 of the cannula 9. The constants $A_1$ and $A_2$ are dependent on the size of the tubing 7 and the size and design of the arthroscope 8 and inflow cannula 9, and therefore care must be taken so that variations in design or manufacturing of the different components do not significantly affect the overall pressure vs. flow relationship, equation D, over the desired ranges. If changes do occur, then processor 13 will be provided with software that will update the processor with the different constants $A_1$ and $A_2$.

Although this is not the presently preferred embodiment, if one were able to directly measure both the flow rate, $Q_{in}$, and pressure, $P_s$, then $P_c$ could be estimated from equation 2 directly, (2) $P_c = P_s - A_1 Q_{in}^2 - A_2 Q_{in}$.

Alternatively, the total pressure drop through the system, ($P_t - P_c$) could be used, which equals $P_1$ plus $P_2$ and can be represented as, (E) $P_t - P_c = (A_1 + H_1) Q_{in}^2 + (A_2 + H_2) Q_{in}$ in which case only the flow rate, $Q_{in}$, would be needed to estimate body cavity pressure, $P_c$, because $P_t$ is known as a function of TAC. This was not implemented due to the high cost of using both a pressure sensor and a flow sensor in the system, and because a means was found to estimate the flow, $Q_{in}$, from the known characteristics of the centrifugal pump and tubing 2,7.

The presently preferred embodiment effectively estimates the body cavity pressure, $P_c$, by calculating the pressure drop downstream of the pressure sensor, $P_2$, from the measured pressure drop upstream of the pressure sensor, $P_1$. This is possible because since the flow through the bag 1—tubing 2—pump 4 and the flow through the tubing 7—cannula 9 are the same, there must be a direct relationship between the pressure drop across the bag 1—tubing 2—pump 4, $P_1$, and the pressure drop across the tubing 7—cannula 9, $P_2$. Since $P_2$ is a function of flow, $Q_{in}$, and $P_1$ is also a function of flow, $Q_{in}$, then $P_2$ must be a function of $P_1$ by the relationship (F) $P_2 = k(P_1)$ which can be predetermined and stored in the program memory for processor 13.

Pressure signal processor 13 receives a pressure signal, $P_s$, from pressure transducer 257 via line 12. Pressure signal processor 13 scales pressure signal $P_s$ to obtain a pressure value in units of mmHg pressure (G) $P_s(\text{mmHg}) = P_s/16$.

Pressure signal processor 13 also receives a tachometer signal, TAC, from tachometer 406 from line 42d. Pressure signal processor 13 calculates the zero flow pump pressure, $P_z$, using equation A, (A) $P_z = f(TAC) = G_1(TAC)^2 + G_2(TAC)$ and then calculates the total zero flow pump pressure, $P_t$, using equation B, where $P_0$ is the known height of bag 1 above pump 4:

(B) $P_t = P_z + P_0 = G_1(TAC)^2 + G_2(TAC) + P_0$.

By definition $P_1$ is the pressure drop upstream of the pressure sensor, as described by equation C, (C) $P_1 = P_t - P_s$ (mmHg).

From equation D, $P_2 = P_s - P_c$, and from equation F, joint pressure $P_c$ can be defined in terms of the calculatable pressure drop $P_1$ by, (G) $P_c = P_s - k(P_1)$ which can then be sent via 32a to be represented in pressure display 5b.

Pressure signal processor 13 also communicates with pressure controller 40 via lines 32 and 32b. Pressure controller 40 receives the values for $P_1$ from pressure signal processor 13 and calculates the total pressure drop, $P_d$, through the pump, tubing and cannula by, (H) $P_d = P_1 + P_2 = P_1 + k(P_1)$.

A running average of 16 calculations per second of $P_d$ is maintained to filter out turbulent noise from the motor 4a. From equation E and knowing the desired set pressure, $P_{set}$, pressure controller 40 calculates the required peak pump pressure, $P^1_z$, to overcome the total pressure drop, $P_d$, through the system by, (I) $P^1_z = P_{set} + P_d - P_0$ Because a centrifugal pump cannot produce negative pressures, $P^1_z$ is bounded to positive values. The TARGET tachometer speed is calculated by solving equation B for TAC, which can be written as $$TAC^1 = TARGET = \frac{-G_1 + \sqrt{G_1^2 + 4G_1 P_z^1}}{2G_2} \quad (J)$$

Since $P^1_z$ is known from equation I, equation J can be solved for TARGET. The TARGET pump speed is then sent to the motor speed controller 407 via lines 41 and 61. If TARGET is more than 100, then pressure controller 40 produces a TARGET signal equal to 100, to maintain a maximum pump speed of 4000 RPM, since for the motor 4a used RPM=40 TAC.

It is presently preferred to solve equations A and I by means of a lookup table stored in memory listing values of $P_z$ and their corresponding TAC values.

To summarize, processor 13 and pressure controller 40 calculate the TARGET speed of motor 406a and hence the speed of pump 4 using as inputs the motor speed, TAC, the sensed pressure, $P_s$, and the set pressure, $P_{set}$, based upon the pressure drops upstream of the sensor to the fluid supply and downstream of the sensor to the inflow cannula tip.

In the preferred embodiment described, motor 4a is a brushless, three-phase DC motor, obtained from BEI KIMCO Magnetics Division, San Marcos, Calif., Part No. DIH 23-20-BBNB, controlled by a microprocessor. While conventional microprocessor controls can be used, it is presently preferred to use the brushless motor control system described in the copending application of Kenneth W. Krause, Ser. No. Ser. No. 867,871 filed concurrently herewith, and entitled Brushless Motor Control System.

Cassette 250 is shown in FIG. 17 in its vertical position as viewed from the rear. For clarity, the front and rear covers 262, 263 (FIG. 18) have been omitted from FIG. 17.

Cassette 250 is made of molded plastic and houses the centrifugal inflow pump 4 disposed vertically, rather than horizontally as in cassette 200 (FIGS. 11–12). Centrifugal inflow pump 4 in cassette 250 is identical to centrifugal inflow pump 4 in cassette 200.

Figure 18:
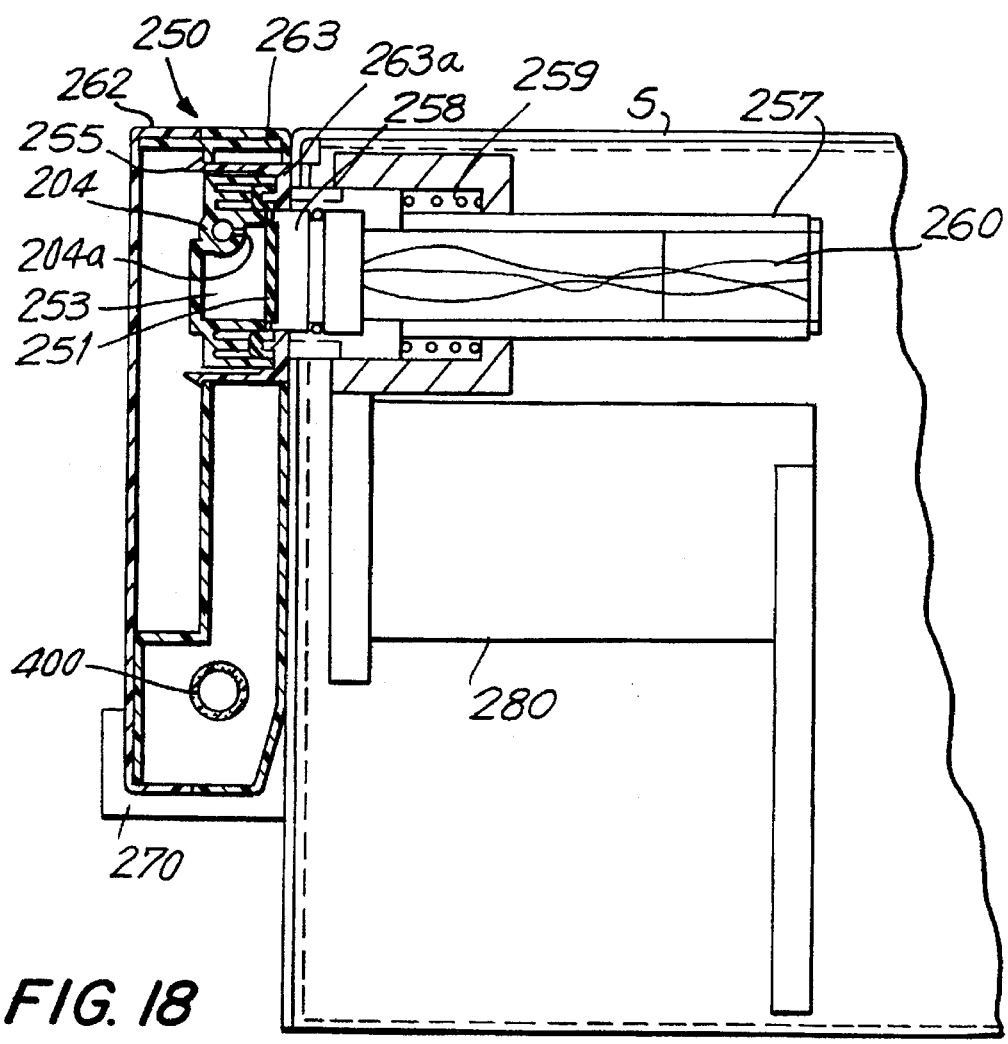
FIG. 18 is a view in section taken along lines 18—18 in FIG. 17.

Within cassette 250 is pump chamber 202 and inlet and outlet conduits 203, 204 connected between pump inlet 205 and pump outlet 206, respectively, and chamber 202. Pump 4 is composed of elements 207–210 as described before and is driven by motor 4a and its elements 300–303 as described before, except that the motor 4a is mounted horizontally, (not shown) in motor support 280 (FIG. 18). Motor 4a drives pump 4 in the cassette 250 in the same manner as described above. Rear cover 263 of the cassette 250 (FIG. 18) has an aperture (not shown) to allow the horizontally mounted motor 4a to be closely adjacent the wall portion 250a (FIG. 17) and hence adjacent to pump 4.

Figure 17A:
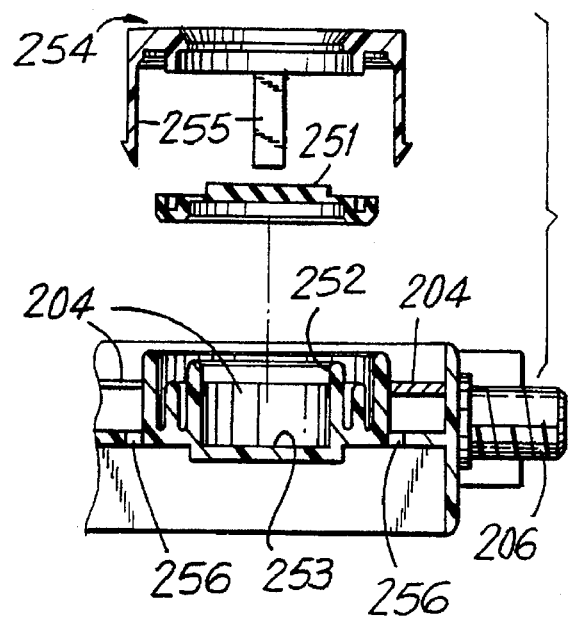
FIG. 17A is a detail exploded view, in section, of a portion of the pump cassette shown in FIG. 17.

Cassette 250 is provided with a thin, flexible diaphragm 251 suitably made of silicone rubber that closes the open end 252 (FIG. 17A) of chamber 253. Flexible diaphragm 251 is securely held in place by clamp 254 by locking the legs 255 into slots 256. Rear cover 263 (FIG. 18) has an aperture 263a exposing the clamp 254 and diaphragm 251. As best seen in FIGS. 17 and 18, a tap hole or channel 204a in outlet conduit 204 permits liquid under pressure delivered by pump 4 to enter chamber 253, thereby exerting a pressure on diaphragm 251 equal to the output static pressure of pump 4, which is inversely related to flow through conduit 204.

Cassette 250 is mounted vertically on the outside of fluid management unit 5 by means of brackets 270, 271 (FIGS. 18, 19A, 19B) such that the rear cover 263 of cassette 250 rests flush against the unit 5, aligned by pins 264. Within unit 5 is a pressure transducer 257 (FIG. 18), whose pressure-sensing element 258 is urged by spring 259 into contact with the diaphragm 251. The relatively small hole 204a and large chamber 253 filled with liquid and air tends to damp high frequency pressure variations of liquid delivered by pump 4 due to flow turbulence. The output of pressure transducer 257 is fed by wires 260 to the input of pressure signal processor 13.

Cassette 250 (FIG. 17) also includes a length of resilient silicone tubing 400 held between connectors 400a and 400b. Tubing 16 and 20, shown in phantom lines, connects tubing 400 to the tool 15 and the suction source 403 (via waste tanks 401, 402), respectively.

Figure 19B:
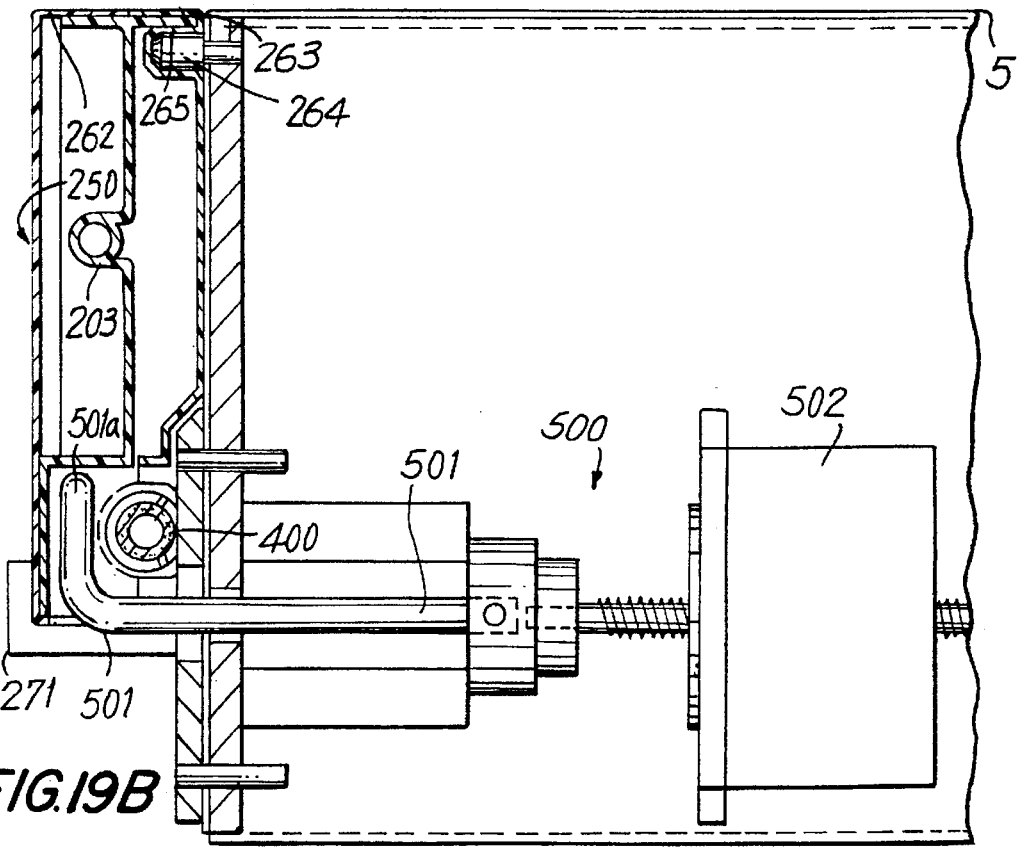
FIGS. 19A and 19B are views in section taken along lines 19—19 in FIG. 17.
Figure 19A:
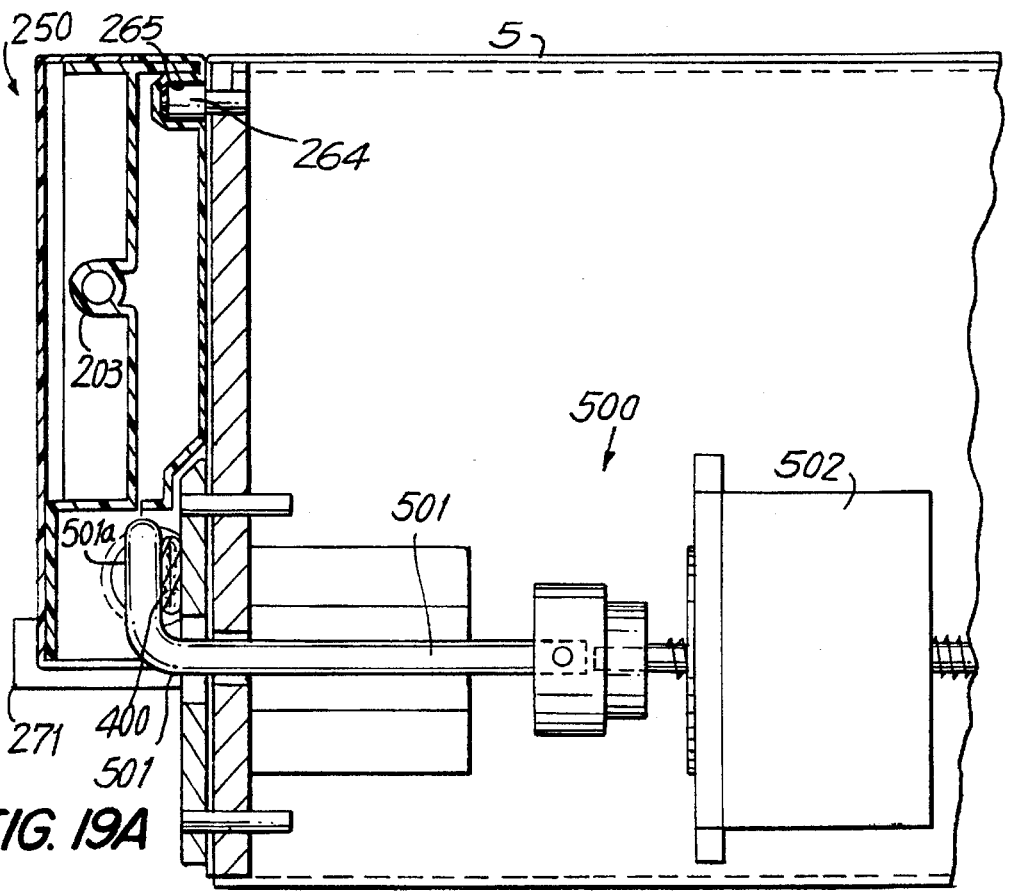

Pinch valve 500 includes an arm 501 that is reciprocated between its normally closed position (FIG. 19A) and its fully open position (FIG. 19B), by the linear actuator motor 502, which, in turn, is controlled by the pinch valve controller 404 and AND gate 60b, as described above. Thus, the normally closed, fully open and intermediate positions of arm 501 are determined by the blade selected for tool 15 and the speed of the tool motor. Linear actuator motor 502 is located inside the fluid management unit 5 with arm 501 extending out of the side wall of unit 5 as shown. While FIGS. 19A and 19B show tubing 400 fully closed and fully open, as discussed above, the "closed" and "open" positions may be less than fully closed or fully open, as desired. Rear cover 263 is slotted to allow the arm to freely move between its open and closed positions.

Before power is initially supplied to the motor 502, arm 501 is fully extended (FIG. 19B) to allow the cassette 250 to be inserted in position on fluid management unit 5. As cassette 250 is lowered into place onto brackets 270,271, tubing 400 will fit behind the finger 501a. A pair of alignment pins 264 on fluid management unit 5 are arranged to fit into recesses 265 in rear cover 263 when cassette 257 is in its proper position. (FIGS. 19A, 19B). After the cassette 250 is snapped in place, the tubing 16, 20 is connected. When power is supplied to the fluid management unit 5, motor 502 moves arm 501 to its normally closed position.

FIG. 20 shows a disposable operative cannula 600 having body portion 601, opposed proximal and distal ends 602, 603, and internal bore 604 extending from end to end. The body portion 601 is provided with spaced apart, external circumferential ribs 614. Sealing members 605,606 which are suitably made of silicone rubber, are secured to distal end 602 to seal the bore 604. Member 605 has a circular aperture 605a therein for sealingly engaging a tool, such as a powered shaver, inserted into cannula 600. Member 606 has sealing elements 606a,606b on either side of slit 606c. Slit 606c is shown as a straight slit, but Y-shaped slits etc. may be used.

Removal of a tool from cannula 600 or inserting a switching stick through cannula 600 from the distal end 603 to the proximal end 602 will cause elements 606a,606b to flex toward member 605. Member 606 is therefore spaced distally of member 605 by a distance that prevents extrusion of elements 606a,606b through aperture 605a. Accordingly, since sealing elements 606a,606b are unsupported by member 605, they must be sufficiently thick to be stiff enough to withstand the back pressure of the liquid in cannula 600, such as about 0.075 inches thick.

If desired, member 605 can be provided with the slit and member 606 with the circular aperture (not shown). In such a case, the sealing elements 606a,606b must be spaced from member 605 to prevent extrusion of elements 606a,606b through aperture 605a when a tool is inserted into cannula 600.

Cannula 600 includes conduit 607 for aspirating liquid from cannula 600 or for supplying liquid to cannula 600. In either case, push valve member 608 will be pushed through fitting 609 from the closed position shown in FIG. 21 to its fully open position (not shown) in which transverse bore 610 is aligned with bores 611,612 in conduit 607 and fitting 609, respectively. Cannula 600 is conveniently molded from suitable plastics. Push valve 608 is suitably molded from silicon rubber, preferably with a hardness greater than Shore A 70. Push valve 608 is color coded such that the red end 608a is showing when valve 608 is closed, and the green end 608b is showing when valve 608 is open.

Cannula 600 desirably includes a circular groove 613 formed in circular body portion 601 near the distal end 603. If the surgeon desires a shorter cannula 600, the body portion can be cut through the groove 613 leaving a shorter cannula having a tapered tip.

Figure 22:
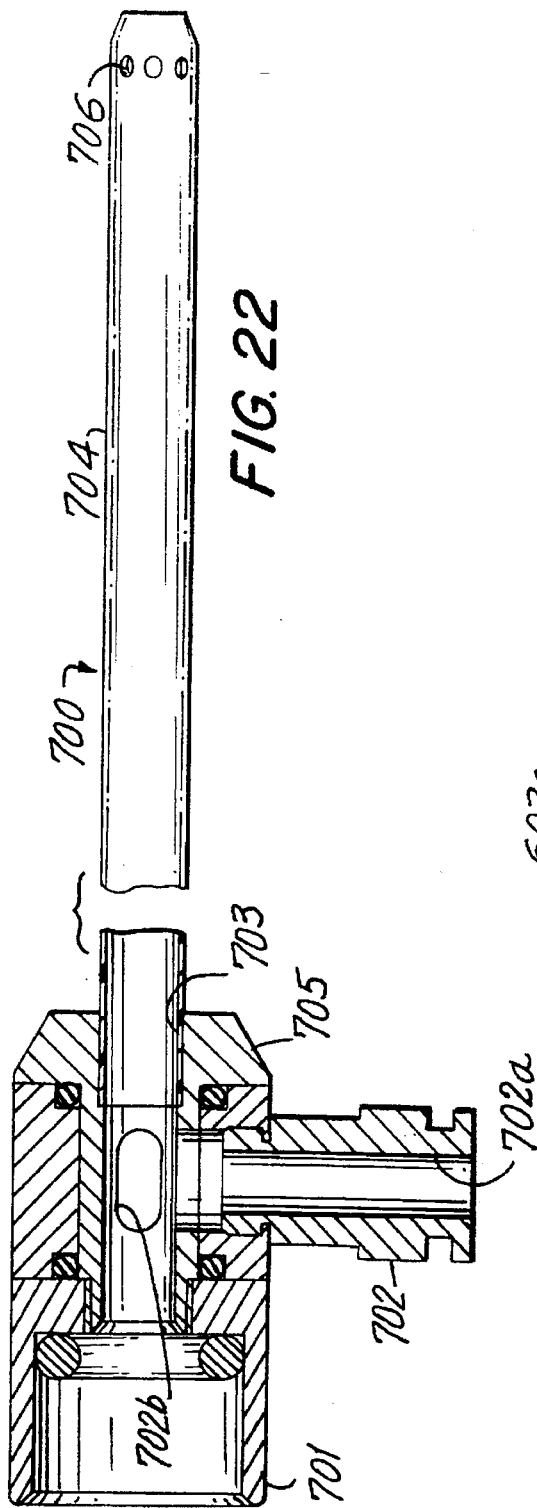
FIG. 22 is a view in section of an adaptor.

FIG. 22 shows a diagnostic cannula 700 having a body 701 and a rotatably mounted inlet 702 that communicates with the internal bore 703 via inlet bore 702a and apertures 702b. Diagnostic inflow cannula 700 is different from inflow cannula assembly 9 described earlier. Without extender 9b, cannula 700 permits the surgeon to reach deeper into the surgical site, which is helpful specifically for shoulder arthroscopy. Although different in application, cannula 700 and cannula assembly 9 have identical pressure vs. flow characteristics, as is required for pressure signal processor 13.

For portal interchangability, cannula 600 is available with an inner diameter suitable for inserting inflow cannula 700 through cannula 600. For example, an endoscope may be first inserted and locked into cannula 700 and remain assembled throughout the surgical procedure. If the surgeon has two operative cannulas 600 in place in the body, one can be used for a tool 15 and the other for the inflow cannula 700. The inflow cannula 700 and endoscope assembly is inserted through sealing members 605,606 until the distal end 703 of body 701 abuts the seal member 605. Push valve member 608 is moved to the closed position. Inflow liquid flows through bore 702a and exits tube 704 through apertures 702b and the annulus between the endoscope and the tube 705. The fluid and operative debris within the surgical site is removed either through the suction adapter on the surgical tool, or can be removed through conduit 607 of operative cannula 600 being used with the surgical tool, in which case push valve member 608 is moved to the open position.

Figure 23:
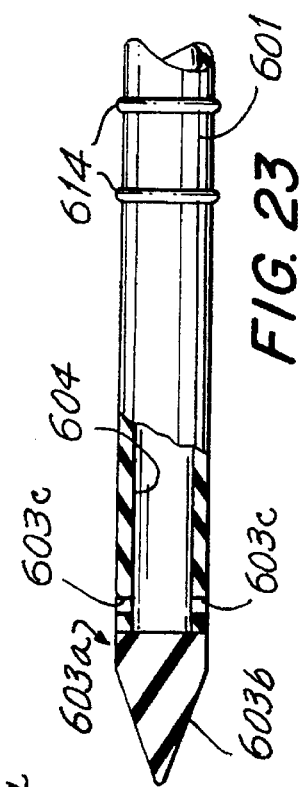
FIG. 23 is a detail view, partly in section, of a modified distal obturator tip for the operative cannula of FIG. 20.

FIG. 23 shows a modified distal tip for the operative cannula of FIG. 20. Thus, the cannula 600 of FIG. 20 has a tapered distal end 603, with internal bore 604 extending through body 601 from the proximal end 605 to and through the distal end 603. In FIG. 23, however, cannula 600 terminates in the distal end 603a which has a tapered obturator tip 603b closing the internal bore 604. Liquid exits internal bore 604 via apertures 603c spaced circumferentially about body 601 just upstream of obturator tip 603b. With this modified distal end 603a, the cannula 600 acts as its own obturator and can be directly advanced through the body without the use of a separate obturator.

Figure 24:
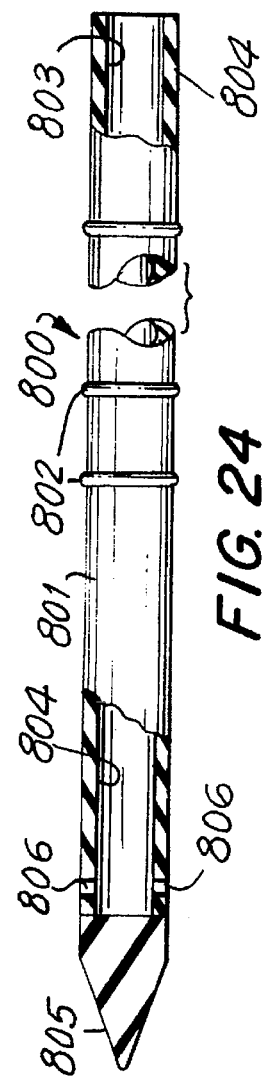
FIG. 24 is a plan view, partly in section, of an obturator cannula of the invention.

FIG. 24 shows a further cannula 800 having a body portion 801 with external ribs 802. An internal bore 803 extends from the proximal end 804 through the body portion 801, with tapered obturator tip 805 closing the bore 803. Liquid exits internal bore 803 via apertures 805. Cannula 800 is made of suitable plastic and can also be advanced into the body without the need for a separate obturator.

We claim:

1. Apparatus for supplying liquid under pressure to a body cavity and establishing a predetermined body cavity pressure during an endoscopic procedure, which comprises:

a) a centrifugal inflow pump for supplying liquid at a pressure suitable for said predetermined body cavity pressure:

b) means for generating a body cavity pressure signal representing the pressure in said body cavity comprising pressure sensor means in communication with liquid under pressure delivered by said centrifugal inflow pump at a location upstream of said body cavity and pressure signal processing means for calculating the value of the pressure in said body cavity from said sensed pressure and for generating a calculated body cavity pressure signal as said body cavity pressure signal;

c) conduit means for communicating said centrifugal inflow pump with said body cavity to deliver liquid under pressure to said body cavity;

d) control means responsive to said body cavity pressure signal for increasing or decreasing the pressure of said liquid delivered by said centrifugal inflow pump to thereby maintain said body cavity pressure at said predetermined pressure;

e) said centrifugal inflow pump, when supplying said liquid at said suitable pressure, having an outflow flow rate that is inherently inversely responsive to changes in said body cavity pressure;

f) a liquid outflow cannula for insertion into said body cavity; and g) a source of suction communicating with said liquid outflow cannula for aspirating liquid from said body cavity via said liquid outflow cannula.

2. Apparatus according to claim 1, wherein said source of suction is a suction pump.

3. Apparatus according to claim 1, wherein tubing means connects said source of suction to said liquid outflow cannula and means is provided selectively to crimp said tubing and thus selectively restrict flow of liquid aspirated from said body cavity.

4. Apparatus according to claim 1, wherein said pressure sensor means comprises a pressure transducer means and an operative pressure-sensing diaphragm, and said pressure signal generating means includes channel means for directing a column of liquid from liquid flowing through said conduit means to said diaphragm.

5. Apparatus according to claim 4, wherein said pressure sensor means comprises a chamber having an open end, a thin, flexible diaphragm closing said open end, channel means for directing liquid delivered from said liquid supply means to said chamber, and pressure transducer means in operative contact with said flexible diaphragm.

6. Apparatus according to claim 1, wherein said location of said pressure sensor means is adjacent the outlet of said centrifugal inflow pump.

7. Apparatus according to claim 6, wherein said pressure sensor means comprises a chamber having an open end, a thin, flexible diaphragm closing said open end, channel means for directing liquid delivered from said pump outlet to said chamber, and pressure transducer means in operative contact with said flexible diaphragm.

* * * * *